United States Patent
El Qacemi et al.

(10) Patent No.: US 9,867,375 B2
(45) Date of Patent: Jan. 16, 2018

(54) METHODS OF PEST CONTROL IN SOYBEAN

(75) Inventors: Myriem El Qacemi, Stein (CH); Jerome Yves Cassayre, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/418,213

(22) PCT Filed: Jul. 31, 2012

(86) PCT No.: PCT/EP2012/064937
§ 371 (c)(1),
(2), (4) Date: Apr. 1, 2015

(87) PCT Pub. No.: WO2014/019609
PCT Pub. Date: Feb. 6, 2014

(65) Prior Publication Data
US 2015/0237862 A1    Aug. 27, 2015

(51) Int. Cl.
*A01N 43/653* (2006.01)
*A01N 43/56* (2006.01)
(Continued)

(52) U.S. Cl.
CPC ............. *A01N 53/00* (2013.01); *A01N 43/08* (2013.01); *A01N 43/36* (2013.01); *A01N 43/56* (2013.01);
(Continued)

(58) Field of Classification Search
None
See application file for complete search history.

(56) References Cited

FOREIGN PATENT DOCUMENTS

| WO | 2007/070606 A2 | 6/2007 |
| WO | 2007/075459 A2 | 7/2007 |

(Continued)

OTHER PUBLICATIONS

Saluso et al., Neotropical Entomology, vol. 40(6), pp. 704-705, 2011.*

(Continued)

*Primary Examiner* — Savitha Rao
*Assistant Examiner* — Gregg Polansky
(74) *Attorney, Agent, or Firm* — R. Kody Jones

(57) ABSTRACT

The present invention provides methods comprising applying to a crop of soybean plants, the locus thereof, or propagation material thereof, a compound of formula (I) wherein —$B^1$—$B^2$—$B^3$— is —C=N—O—, —C=N—$CH_2$—, —N—$CH_2$—$CH_2$—, or —C=C—O—; $R^1$ is trifluoromethyl, difluoromethyl or chlorodifluoromethyl; $R^2$ is group (X) wherein $X^2$ is C—$X^6$ or nitrogen; $X^1$, $X^3$ and $X^6$ are independently hydrogen, halogen or trihalomethyl, wherein at least one of $X^1$, $X^3$ and $X^6$ is not hydrogen; A is selected from group (A1) to (A4) and $Y^1$, $Y^2$, $Y^3$, $R^5$ and $R^8$ are as defined in claim 1. The methods are preferably for the control of stinkbugs, in particular *Euschistus*.

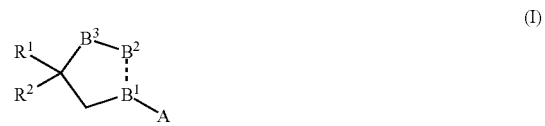

(I)

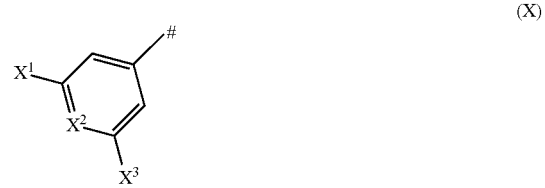

(X)

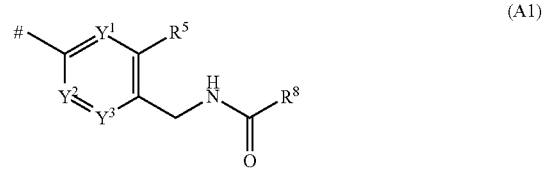

(A1)

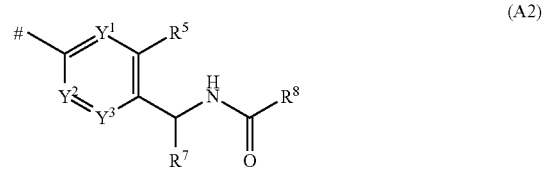

(A2)

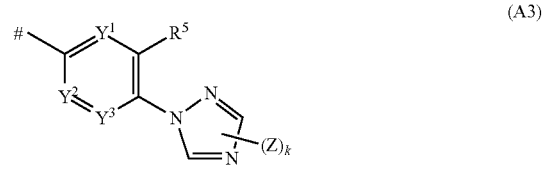

(A3)

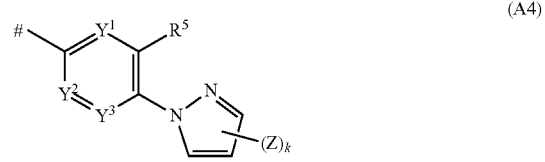

(A4)

1 Claim, No Drawings

(51) Int. Cl.
  *A01N 43/80*   (2006.01)
  *A01N 53/00*   (2006.01)
  *A01N 43/08*   (2006.01)
  *A01N 43/36*   (2006.01)
  *C07D 207/09*  (2006.01)
  *C07D 207/20*  (2006.01)
  *C07D 261/04*  (2006.01)
  *C07D 403/10*  (2006.01)
  *G06Q 30/00*   (2012.01)

(52) U.S. Cl.
  CPC ........... *A01N 43/653* (2013.01); *A01N 43/80* (2013.01); *C07D 207/09* (2013.01); *C07D 207/20* (2013.01); *C07D 261/04* (2013.01); *C07D 403/10* (2013.01); *G06Q 30/018* (2013.01)

(56) References Cited

FOREIGN PATENT DOCUMENTS

| | | |
|---|---|---|
| WO | 2008/150393 A1 | 12/2008 |
| WO | 2009/045999 A1 | 4/2009 |
| WO | 2009/051956 A2 | 4/2009 |
| WO | WO 2009/097992 A1 * | 8/2009 |

OTHER PUBLICATIONS

International Search Report dated Aug. 28, 2013 for International Patent Application No. PCT/EP2012/064937.

* cited by examiner

METHODS OF PEST CONTROL IN SOYBEAN

RELATED APPLICATION INFORMATION

This application is a 371 of International Application No. PCT/EP2012/064937, filed 31 Jul. 2012, the contents of which are incorporated herein by reference herein.

The present invention relates to methods of pest control in soybean crops.

Stink bugs (*Hemiptera Pentatomidae*) are true bugs which can be significant pests when present in large numbers. The nymphs and adults have piercing mouthparts which most use to suck sap from plants. According to Stewart et al., Soybean Insects-Stink bugs, University of Tennessee Institute of Agriculture, W200 09-0098, stink bugs are probably the most common pest problem in soybean. Although they may feed on many parts of the plant, they typically target developing seed including the pods, meaning that injury to soybean seed is the primary problem associated with stink bug infestations.

Of the complex of sucking bugs that occur in cultivation, the brown stinkbug *Euschistus heros* is currently considered to be the most abundant species in northern Parana to Central Brazil (Corrêa-Ferreira & Panizzi, 1999), and is a significant problem in soybean (Schmidt et al., 2003). The bugs occur in soybeans from the vegetative stage and are harmful from the beginning of pod formation until grain maturity. They cause damage to the seed (Galileo & Heinrichs 1978a, Panizzi & Slansky Jr., 1985) and can also open the way to fungal diseases and cause physiological disorders, such as soybean leaf retention (Galileo & Heinrichs 1978, Todd & Herzog, 1980).

Control of stinkbugs in soybean is often vital to prevent significant economic damage. Insecticides commonly used to control stinkbugs include pyrethroids, neonicotinoids and organophosphates, although pyrethroid insecticides are usually the method of choice for controlling stink bugs in soybean. However, there are increasing problems with insecticide resistance, particularly in brown stink bug populations and particularly to pyrethroids. *Euschistus heros* can also be difficult to manage using organophosphates or endosulfan (Sosa-Gomez et al., 2009). There is therefore a need for effective alternative methods of controlling stinkbugs in soybean.

Compounds that are insecticidally, acaricidally, nematicidally and/or moluscicidally active by antagonism of the gamma-aminobutyric acid (GABA)-gated chloride channel, and which comprise a partially saturated heterocycle that is substituted by a haloalkyl substituent and one or two optionally substituted aromatic or heteroaromatic rings, represent a new class of pesticides that are described for example in Ozoe et al. Biochemical and Biophysical Research Communications, 391 (2010) 744-749. Compounds from this class are broadly described in WO 2005/085216 (EP1731512), WO 2007/123853, WO 2007/075459, WO2009/002809, WO 2008/019760, WO 2008/122375, WO 2008/128711, WO 2009/097992, WO 2010/072781, WO 2010/072781, WO 2008/126665, WO 2007/125984, WO 2008/130651, JP 2008110971, JP2008133273, JP2009108046, WO2009/022746, WO 2009/022746, WO 2010/032437, WO2009/080250, WO2010/020521, WO2010/025998, WO2010/020522, WO2010/084067, WO2010/086225, WO2010/149506 and WO2010/108733.

It has now surprisingly been found that particular insecticides from this new class of gamma-aminobutyric acid (GABA)-gated chloride channel antagonists are highly effective at controlling stinkbugs, and in some cases can provide greater control than the current market standard. It has also surprisingly been found that these compounds exhibit significantly higher activity against stinkbugs than structurally similar compounds. These compounds therefore represent an important new solution for safeguarding soybean crops from stinkbugs, particularly where stink bugs are resistant to current methods.

In a first aspect the invention provides a method comprising applying to a crop of soybean plants, the locus thereof, or propagation material thereof, a compound of formula I

wherein —$B^1$—$B^2$—$B^3$— is —C=N—O—, —C=N—CH$_2$—, —N—CH$_2$—CH$_2$—, or —C=C—O—;

$R^1$ is trifluoromethyl, difluoromethyl or chlorodifluoromethyl;

$R^2$ is group X

$X^2$ is C—$X^6$ or nitrogen;

$X^1$, $X^3$ and $X^6$ are independently hydrogen, halogen or trihalomethyl, wherein at least one of $X^1$, $X^3$ and $X^6$ is not hydrogen;

A is selected from group A1 to A4

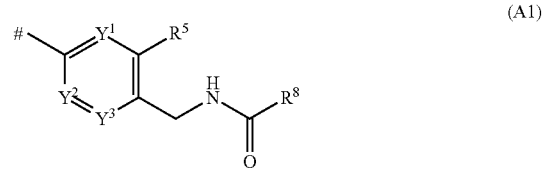

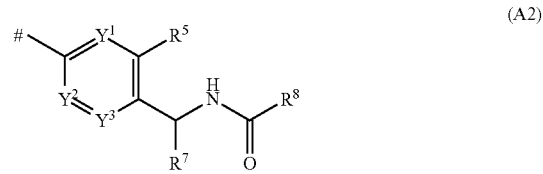

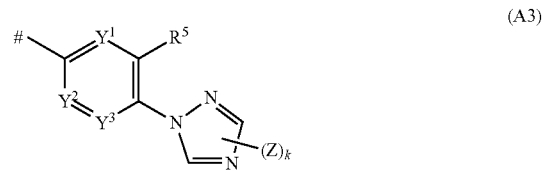

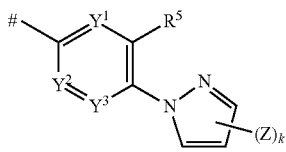
(A4)

$Y^1$ is C—$R^6$, CH or nitrogen;
$Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$R^5$ is hydrogen, halogen, cyano, nitro, $NH_2$, $C_1$-$C_4$alkyl, $C_1$-$C_4$haloalkyl, $C_3$-$C_5$cycloalkyl, $C_3$-$C_5$halocycloalkyl, $C_1$-$C_2$alkoxy, or $C_1$-$C_2$haloalkoxy;
$R^6$ when present together with $R^5$ forms a —CH=CH—CH=CH— bridge;
$R^7$ is $C_1$-$C_4$alkyl;
$R^8$ is $C_1$-$C_4$alkyl, $C_1$-$C_4$haloalkyl, $C_1$-$C_4$alkoxy($C_1$-$C_4$)alkyl, $C_1$-$C_4$alkylthio($C_1$-$C_4$)alkyl, $C_1$-$C_4$alkylsulfinyl($C_1$-$C_4$)alkyl, $C_1$-$C_4$alkylsulfonyl($C_1$-$C_4$)alkyl, $C_3$-$C_6$cycloalkyl, $C_3$-$C_6$cycloalkyl($C_1$-$C_4$)alkyl-, or tetrahydrofuranyl;
each Z is independently halogen, $C_1$-$C_{12}$alkyl or $C_1$-$C_{12}$alkyl substituted by one to five $R^{12}$, nitro, $C_1$-$C_{12}$alkoxy or $C_1$-$C_{12}$alkoxy substituted by one to five $R^{12}$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol;
each $R^{12}$ is halogen, cyano, nitro, hydroxy, $C_1$-$C_8$alkoxy-, $C_1$-$C_8$haloalkoxy-, mercapto, $C_1$-$C_8$alkylthio-, or $C_1$-$C_8$haloalkylthio; and
k is 0, 1, 2 or 3.

In a further aspect the invention provides a method of controlling and/or preventing infestation of stinkbugs in soybean comprising applying to a crop of soybean plants, the locus thereof, or propagation material thereof, a compound of formula I. The stinkbugs may be those that are resistant to one or more other insecticides.

In a further aspect the invention provides a method of controlling and/or preventing infestation of stinkbugs in a crop of useful plants comprising applying to a crop of useful plants, the locus thereof, or propagation material thereof, a compound of formula I. The stinkbugs may be those that are resistant to one or more other insecticides.

In a further aspect the invention provides use of a compound of formula I for control of stinkbugs in a crop of useful plants. The use may be for controlling stinkbugs that are resistant to one or more other insecticides.

In a further aspect the invention provides a method of controlling and/or preventing infestation of insects from the genus Euschistus in a crop of useful plants comprising applying to a crop of useful plants, the locus thereof, or propagation material thereof, a compound of formula I. The insects from the genus Euschistus may be those that are resistant to one or more other insecticides.

In a further aspect the invention provides use of a compound of formula I for control of insects from the genus Euschistus in a crop of useful plants. The use may be for controlling insects from the genus Euschistus that are resistant to one or more other insecticides.

In a further aspect the invention provides a method of controlling and/or preventing infestation of insects from the genus Euschistus in a crop of soybean plants comprising applying to a crop of soybean, the locus thereof, or propagation material thereof, a compound of formula I. The insects from the genus Euschistus may be those that are resistant to one or more other insecticides.

In a further aspect the invention provides use of a compound of formula I for control of insects from the genus Euschistus in a crop of soybean plants. The use may be for controlling insects from the genus Euschistus that are resistant to one or more other insecticides.

In a further aspect the invention provides a method of controlling and/or preventing infestation of Euschistus heros in a crop of useful plants comprising applying to a crop of useful plants, the locus thereof, or propagation material thereof, a compound of formula I. The Euschistus heros may be resistant to one or more other insecticides.

In a further aspect the invention provides use of a compound of formula I for control of Euschistus heros in a crop of useful plants. The use may be for controlling Euschistus heros that is resistant to one or more other insecticides.

In a further aspect the invention provides a method of controlling and/or preventing infestation of Euschistus heros in a crop of soybean plants comprising applying to a crop of soybean, the locus thereof, or propagation material thereof, a compound of formula I. The Euschistus heros may be resistant to one or more other insecticides.

In a further aspect the invention provides use of a compound of formula I for control of Euschistus heros in a crop of soybean plants. The use may be for controlling insects Euschistus heros that are is resistant to one or more other insecticides.

Stinkbugs that are resistant to one or more other insecticides are preferably resistant to pyrethroid, neonicotinoids and/or organophosphates, more preferably pyrethroid insecticides.

In a further aspect the invention provides a method for obtaining regulatory approval for the use of one or more of a compound of formula I to control stinkbugs, in particular the genus Euschistus and in particular the species Euschistus heros, and in particular in soybean plants, comprising at least one step of referring to, submitting or relying on biological data showing that said active ingredient reduces insect pressure.

The compounds of the invention may exist in different geometric or optical isomers or tautomeric forms. This invention covers all such isomers and tautomers and mixtures thereof in all proportions as well as isotopic forms such as deuterated compounds. The compounds of the invention may contain one or more asymmetric carbon atoms, for example, at the C($R^1$)$R^2$ group, and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. Unless otherwise stated the alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Cycloalkyl groups or carbocyclic rings can be in mono- or bi-cyclic form and are, for example, cyclopropyl, cyclobutyl, cyclohexyl. The cycloalkyl groups are preferably $C_3$-$C_6$ cycloalkyl groups.

The preferences for $B^1$, $B^2$, $B^3$, $R^1$, $R^2$, $Y^1$, $Y^2$, $Y^3$, $R^5$, $R^6$, $R^7$, $R^8$, $R^{12}$, $X^1$ $X^2$, $X^3$, $Z$ and $k$ are, in any combination, as described below.

Preferably $R^1$ is trifluoromethyl, or chlorodifluoromethyl, most preferably trifluoromethyl.

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl.

In one group of compounds $R^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl, 3,5-dichloro-4-fluorophenyl- or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, most preferably $R^5$ is hydrogen, cyano, chloro, bromo, fluoro, methyl, or trifluoromethyl.

Preferably $R^8$ is $C_1$-$C_4$alkyl, $C_1$-$C_4$haloalkyl, $C_1$-$C_4$alkyl-O—$CH_2$—, $C_1$-$C_4$haloalkyl-O—$CH_2$—, $C_3$-$C_6$cycloalkyl, $C_3$-$C_6$cycloalkyl-$CH_2$—, $C_1$-$C_4$alkyl-S(O)—$CH_2$—, $C_1$-$C_4$alkyl-S($O_2$)—$CH_2$—, more preferably $C_1$-$C_4$alkyl, $C_1$-$C_4$alkyl-O—$CH_2$—, $C_1$-$C_4$alkyl-S—$CH_2$—, $C_1$-$C_4$alkyl-SO—$CH_2$—, $C_1$-$C_4$alkyl-$SO_2$—$CH_2$—, $C_3$-$C_4$cycloalkyl, or $C_3$-$C_4$cycloalkyl-$CH_2$—, most preferably $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, most preferably each Z is independently hydrogen, cyano, halogen, methyl, halomethyl, methoxy or halomethoxy, most preferably cyano or trifluoromethyl.

Each $R^{12}$ is preferably bromo, chloro, fluoro, methoxy, or methylthio, most preferably chloro, fluoro, or methoxy Preferably k is 0 or 1.

In one group of compounds —$B^1$—$B^2$—$B^3$— is —C═N—O—.

In another group of compounds —$B^1$—$B^2$—$B^3$— is —C═N—$CH_2$—.

In another group of compounds —$B^1$—$B^2$—$B^3$— is —N—$CH_2$—$CH_2$—.

In another group of compounds —$B^1$—$B^2$—B— is —C═C—O—.

In another group of compounds $Y^1$ is C—$R^6$ and $R^6$ together with $R^5$ forms a —CH═CH—CH═CH— bridge.

In one embodiment the compound of formula I is a compound of formula IA

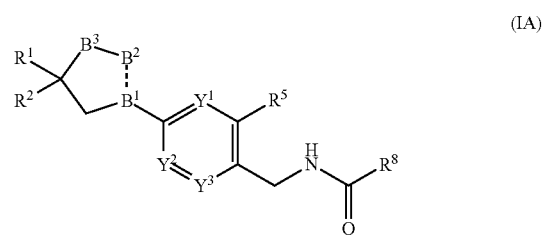

(IA)

wherein $B^1$, $B^2$, $B^3$, $R^1$, $R^2$, $Y^1$, $Y^2$, $Y^3$, $R^5$ and $R^8$ are as defined for a compound of formula I In compounds of formula IA preferred definitions of $B^1$, $B^2$, $B^3$, $R^1$, $R^2$, $Y^1$, $Y^2$, $Y^3$, $R^5$ and $R^8$ are, in any combination, as set out below:

Preferably $R^1$ is trifluoromethyl, or chlorodifluoromethyl, most preferably trifluoromethyl.

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl.

In one group of compounds $R^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, more preferably $R^5$ is hydrogen, cyano, chloro, bromo, fluoro, methyl, or trifluoromethyl, even more preferably hydrogen, chloro, bromo, methyl or trifluoromethyl, most preferably chloro, bromo, fluoro or methyl.

Preferably $R^8$ is $C_1$-$C_4$alkyl, $C_1$-$C_4$haloalkyl, $C_1$-$C_4$alkyl-O—$CH_2$—, $C_1$-$C_4$haloalkyl-O—$CH_2$—, $C_3$-$C_6$cycloalkyl, $C_3$-$C_6$cycloalkyl-$CH_2$—, $C_1$-$C_4$alkyl-S(O)—$CH_2$—, $C_1$-$C_4$alkyl-S($O_2$)—$CH_2$—, more preferably $C_1$-$C_4$alkyl, $C_1$-$C_4$alkyl-O—$CH_2$—, $C_1$-$C_4$alkyl-S—$CH_2$—, $C_1$-$C_4$alkyl-SO—$CH_2$—, $C_1$-$C_4$alkyl-$SO_2$—$CH_2$—, $C_3$-$C_4$cycloalkyl, or $C_3$-$C_4$cycloalkyl-$CH_2$—, most preferably $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In one group of compounds of formula IA —$B^1$—$B^2$—$B^3$— is —C=N—O—.

In another group of compounds of formula IA —$B^1$—$B^2$—$B^3$— is —C=N—O— and $Y^1$ is CH, $Y^2$ is CH, $Y^3$ is CH.

In another group of compounds of formula IA —$B^1$—$B^2$—$B^3$— is —C=N—O—, $Y^1$ is CH, $Y^2$ is CH, $Y^3$ is CH and $R^1$ is $CF_3$.

In another group of compounds of formula IA —$B^1$—$B^2$—$B^3$— is —C=N—O—, $Y^1$ is CH, $Y^2$ is CH, $Y^3$ is CH, $R^1$ is $CF_3$ and $R^5$ is chloro, bromo, fluoro or methyl.

In another group of compounds of formula IA —$B^1$—$B^2$—$B^3$— is —C=N—O—, $Y^1$ is CH, $Y^2$ is CH, $Y^3$ is CH, $R^1$ is $CF_3$, and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —C=N—O—, $Y^1$ is CH, $Y^2$ is CH, $Y^3$ is CH, $R^1$ is $CF_3$, $R^5$ is chloro, bromo, fluoro or methyl and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —C=N—O—, $Y^1$ is CH, $Y^2$ is CH, $Y^3$ is CH, $R^1$ is $CF_3$, $R^5$ is chloro, bromo, fluoro or methyl, $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$— and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IA —$B^1$—$B^2$—$B^3$— is —C=N—$CH_2$—.

In another group of compounds of formula IA —$B^1$—$B^2$—$B^3$— is —C=N—$CH_2$— and $Y^1$ is CH, $Y^2$ is CH, $Y^3$ is CH.

In another group of compounds of formula IA —$B^1$—$B^2$—$B^3$— is —C=N—$CH_2$—, $Y^1$ is CH, $Y^2$ is CH, $Y^3$ is CH and $R^1$ is $CF_3$.

In another group of compounds of formula IA —$B^1$—$B^2$—$B^3$— is —C=N—$CH_2$—, $Y^1$ is CH, $Y^2$ is CH, $Y^3$ is CH, $R^1$ is $CF_3$ and $R^5$ is chloro, bromo, fluoro or methyl.

In another group of compounds of formula IA —$B^1$—$B^2$—$B^3$— is —C=N—$CH_2$—, $Y^1$ is CH, $Y^2$ is CH, $Y^3$ is CH, $R^1$ is $CF_3$, and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —C=N—$CH_2$—, $Y^1$ is CH, $Y^2$ is CH, $Y^3$ is CH, $R^1$ is $CF_3$, $R^5$ is chloro, bromo, fluoro or methyl and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —C=N—$CH_2$—, $Y^1$ is CH, $Y^2$ is CH, $Y^3$ is CH, $R^1$ is $CF_3$, $R^5$ is chloro, bromo, fluoro or methyl and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$— and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IA —$B^1$—$B^2$—$B^3$— is —N—$CH_2$—$CH_2$—.

In another group of compounds of formula IA —$B^1$—$B^2$—$B^3$— is —N—$CH_2$—$CH_2$—, $Y^1$ is CH, $Y^2$ is CH, $Y^3$ is CH.

In another group of compounds of formula IA —$B^1$—$B^2$—$B^3$— is —N—$CH_2$—$CH_2$—, $Y^1$ is CH, $Y^2$ is CH, $Y^3$ is CH and $R^1$ is $CF_3$.

In another group of compounds of formula IA —$B^1$—$B^2$—$B^3$— is —N—$CH_2$—$CH_2$—, $Y^1$ is CH, $Y^2$ is CH, $Y^3$ is CH, $R^1$ is $CF_3$ and $R^5$ is chloro, bromo, fluoro or methyl.

In another group of compounds of formula IA —$B^1$—$B^2$—$B^3$— is —N—$CH_2$—$CH_2$—, $Y^1$ is CH, $Y^2$ is CH, $Y^3$ is CH, $R^1$ is $CF_3$, and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is chloro, bromo, fluoro or methyl and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is chloro, bromo, fluoro or methyl, $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$— and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IA —$B^1$—$B^2$—$B^3$— is —C=C—O—.

In another group of compounds of formula IA —$B^1$—$B^2$—$B^3$— is —C=C—O— and $Y^1$ is CH, $Y^2$ is CH, $Y^3$ is CH.

In another group of compounds of formula IA —$B^1$—$B^2$—$B^3$— is —C=C—O—, $Y^1$ is CH, $Y^2$ is CH, $Y^3$ is CH and $R^1$ is $CF_3$.

In another group of compounds of formula IA —$B^1$—$B^2$—$B^3$— is —C=C—O—, $Y^1$ is CH, $Y^2$ is CH, $Y^3$ is CH, $R^1$ is $CF_3$ and $R^5$ is chloro, bromo, fluoro or methyl.

In another group of compounds of formula IA —$B^1$—$B^2$—$B^3$— is —C=C—O—, $Y^1$ is CH, $Y^2$ is CH, $Y^3$ is CH, $R^1$ is $CF_3$, and $R^8$ is methyl, ethyl, isopropyl, $CH_3$—O—$CH_2$—, $CH_3$—S—$CH_2$—, $CH_3$—S(O)—$CH_2$—, $CH_3$—$SO_2$—$CH_2$—, cyclobutyl, cyclopropyl or cyclopropyl-$CH_2$—.

In another group of compounds of formula IA —B¹—B²—B³— is —C=C—O—, Y¹ is CH, Y² is CH, Y³ is CH, R¹ is CF₃, R⁵ is chloro, bromo, fluoro or methyl, R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—.

In another group of compounds of formula IA —B¹—B²—B³— is —C=C—O—, Y¹ is CH, Y² is CH, Y³ is CH, R¹ is CF₃, R⁵ is chloro, bromo, fluoro or methyl and R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂— and R² is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In another group of compounds of formula IA R⁵ is chloro, bromo, fluoro or methyl and R⁸ methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—.

In another group of compounds of formula IA R⁵ is chloro, bromo, fluoro or methyl; R⁸ methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—, R¹ is CF₃, —B¹—B²—B³— is —C=N—O— or —C=N—CH₂—, Y¹, Y² and Y³ are CH, and R⁵ is chloro or methyl.

In one embodiment the compound of formula I is a compound of formula IB

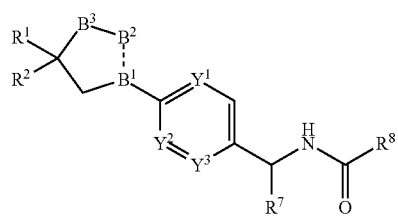

(IB)

wherein B¹, B², B³, R¹, R², Y¹, Y², Y³, R⁷ and R⁸ are as defined for a compound of formula I In compounds of formula IB preferred definitions of B¹, B², B³, R¹, R², Y¹, Y², Y³, R⁷ and R⁸ are, in any combination, as set out below Preferably R¹ is trifluoromethyl, or chlorodifluoromethyl, most preferably trifluoromethyl.

Preferably X¹, X³ and X⁶ are independently hydrogen, halogen or trifluoromethyl, wherein at least two of X¹, X³ and X⁶ are not hydrogen. More preferably X¹, X³ and X⁶ are independently hydrogen, chloro, bromo or trifluoromethyl, wherein at least two of X¹, X³ and X⁶ are not hydrogen. Preferably at least two of X¹, X³ and X⁶ are chloro, bromo or trifluoromethyl.

In one group of compounds R² is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably R² is 3,5-dichloro-phenyl or 3,4,5-trichloro-phenyl, most preferably 3,5-dichloro-phenyl.

Preferably Y¹ is CH, Y² is CH, Y³ is CH, or Y¹ is N, Y² is CH, Y³ is CH, or Y¹ is N, Y² is N, Y³ is CH, or Y¹ is CH, Y² is N, Y³ is CH, or Y¹ is CH, Y² is CH, Y³ is N. Most preferably Y¹ is CH, Y² is CH, and Y³ is CH.

Preferably R⁷ is methyl.

Preferably R⁸ is C₁-C₄alkyl, C₁-C₄haloalkyl, C₁-C₄alkyl-O—CH₂—, C₁-C₄haloalkyl-O—CH₂—, C₃-C₆cycloalkyl, C₃-C₆cycloalkyl-CH₂—, C₁-C₄alkyl-S(O)—CH₂—, C₁-C₄alkyl-S(O₂)—CH₂—, more preferably C₁-C₄alkyl, C₁-C₄alkyl-O—CH₂—, C₁-C₄alkyl-S—CH₂—, C₁-C₄alkyl-SO—CH₂—, C₁-C₄alkyl-SO₂—CH₂—, C₃-C₄cycloalkyl, or C₃-C₄cycloalkyl-CH₂—, most preferably R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—.

In one group of compounds of formula IB —B¹—B²—B³— is —C=N—O—.

In another group of compounds of formula IB —B¹—B²—B³— is —C=N—O— and Y¹ is CH, Y² is CH, Y³ is CH.

In another group of compounds of formula IB —B¹—B²—B³— is —C=N—O—, Y¹ is CH, Y² is CH, Y³ is CH and R¹ is CF₃.

In another group of compounds of formula IB —B¹—B²—B³— is —C=N—O—, Y¹ is CH, Y² is CH, Y³ is CH, R¹ is CF₃ and R⁷ is methyl.

In another group of compounds of formula IB —B¹—B²—B³— is —C=N—O—, Y¹ is CH, Y² is CH, Y³ is CH, R¹ is CF₃, and R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—.

In another group of compounds of —B¹—B²—B³— is —C=N—O—, Y¹ is CH, Y² is CH, Y³ is CH, R¹ is CF₃, R⁷ is methyl and R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂—.

In another group of compounds of formula IB —B¹—B²—B³— is —C=N—O—, Y¹ is CH, Y² is CH, Y³ is CH, R¹ is CF₃, R⁷ is methyl, R⁸ is methyl, ethyl, isopropyl, CH₃—O—CH₂—, CH₃—S—CH₂—, CH₃—S(O)—CH₂—, CH₃—SO₂—CH₂—, cyclobutyl, cyclopropyl or cyclopropyl-CH₂— and R² is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In one group of compounds of formula IB —B¹—B²—B³— is —C=N—CH₂—.

In another group of compounds of formula IB —B¹—B²—B³— is —C=N—CH₂— and Y¹ is CH, Y² is CH, Y³ is CH.

In another group of compounds of formula IB —B$^1$—B$^2$—B$^3$— is —C=N—CH$_2$—, Y$^1$ is CH, Y$^2$ is CH, Y$^3$ is CH and R$^1$ is CF$_3$.

In another group of compounds of formula IB —B$^1$—B$^2$—B$^3$— is —C=N—CH$_2$—, Y$^1$ is CH, Y$^2$ is CH, Y$^3$ is CH, R$^1$ is CF$_3$ and R$^7$ is methyl.

In another group of compounds of formula IB —B$^1$—B$^2$—B$^3$— is —C=N—CH$_2$—, Y$^1$ is CH, Y$^2$ is CH, Y$^3$ is CH, R$^1$ is CF$_3$, and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —C=N—CH$_2$—, Y$^1$ is CH, Y$^2$ is CH, Y$^3$ is CH, R$^1$ is CF$_3$, R$^7$ is methyl and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —C=N—CH$_2$—, Y$^1$ is CH, Y$^2$ is CH, Y$^3$ is CH, R$^1$ is CF$_3$, R$^7$ is methyl, R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$— and R$^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In one group of compounds of formula IB —B$^1$—B$^2$—B$^3$— is —N—CH$_2$—CH$_2$—.

In another group of compounds of formula IB —B$^1$—B$^2$—B$^3$— is —N—CH$_2$—CH$_2$— and Y$^1$ is CH, Y$^2$ is CH, Y$^3$ is CH.

In another group of compounds of formula IB —B$^1$—B$^2$—B$^3$— is —N—CH$_2$—CH$_2$—, Y$^1$ is CH, Y$^2$ is CH, Y$^3$ is CH and R$^1$ is CF$_3$.

In another group of compounds of formula IB —B$^1$—B$^2$—B$^3$— is —N—CH$_2$—CH$_2$—, Y$^1$ is CH, Y$^2$ is CH, Y$^3$ is CH, R$^1$ is CF$_3$ and R$^7$ is methyl.

In another group of compounds of formula IB —B$^1$—B$^2$—B$^3$— is —N—CH$_2$—CH$_2$—, Y$^1$ is CH, Y$^2$ is CH, Y$^3$ is CH, R$^1$ is CF$_3$, and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —N—CH$_2$—CH$_2$—, Y$^1$ is CH, Y$^2$ is CH, Y$^3$ is CH, R$^1$ is CF$_3$, R$^7$ is methyl and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —N—CH$_2$—CH$_2$—, Y$^1$ is CH, Y$^2$ is CH, Y$^3$ is CH, R$^1$ is CF$_3$, R$^7$ is methyl, R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$— and R$^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In one group of compounds of formula IB —B$^1$—B$^2$—B$^3$— is —C=C—O—.

In another group of compounds of formula IB —B$^1$—B$^2$—B$^3$— is —C=C—O— and Y$^1$ is CH, Y$^2$ is CH, Y$^3$ is CH.

In another group of compounds of formula IB —B$^1$—B$^2$—B$^3$— is —C=C—O—, Y$^1$ is CH, Y$^2$ is CH, Y$^3$ is CH and R$^1$ is CF$_3$.

In another group of compounds of formula IB —B$^1$—B$^2$—B$^3$— is —C=C—O—, Y$^1$ is CH, Y$^2$ is CH, Y$^3$ is CH, R$^1$ is CF$_3$ and R$^7$ is methyl.

In another group of compounds of formula IB —B$^1$—B$^2$—B$^3$— is —C=C—O—, Y$^1$ is CH, Y$^2$ is CH, Y$^3$ is CH, R$^1$ is CF$_3$, and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —C=C—O—, Y$^1$ is CH, Y$^2$ is CH, Y$^3$ is CH, R$^1$ is CF$_3$, R$^7$ is methyl and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB —B$^1$—B$^2$—B$^3$— is —C=C—O—, Y$^1$ is CH, Y$^2$ is CH, Y$^3$ is CH, R$^1$ is CF$_3$, R$^7$ is methyl, R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$— and R$^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In another group of compounds of formula IB R$^7$ is methyl, and R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—.

In another group of compounds of formula IB R$^7$ is methyl, R$^8$ is methyl, ethyl, isopropyl, CH$_3$—O—CH$_2$—, CH$_3$—S—CH$_2$—, CH$_3$—S(O)—CH$_2$—, CH$_3$—SO$_2$—CH$_2$—, cyclobutyl, cyclopropyl or cyclopropyl-CH$_2$—, R$^1$ is CF$_3$, —B$^1$—B$^2$—B$^3$— is —C=N—O—, —C=N—CH$_2$— or —N—CH$_2$—CH$_2$—, and Y$^1$, Y$^2$ and Y$^3$ are CH.

In one embodiment the compound of formula I is a compound of formula IC

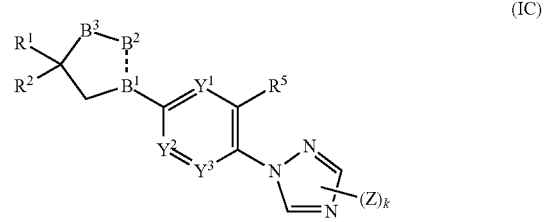

(IC)

wherein B$^1$, B$^2$, B$^3$, R$^1$, R$^2$, Y$^1$, Y$^2$, Y$^3$, R$^5$ Z and k are as defined for a compound of formula I In compounds of formula IC preferred definitions of B$^1$, B$^2$, B$^3$, R$^1$, R$^2$, Y$^1$, Y$^2$, Y$^3$, R$^5$, Z and k are, in any combination, as set out below Preferably R$^1$ is trifluoromethyl, or chlorodifluoromethyl, most preferably trifluoromethyl.

Preferably X$^1$, X$^3$ and X$^6$ are independently hydrogen, halogen or trifluoromethyl, wherein at least two of X$^1$, X$^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl.

In one group of compounds $R^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, even more preferably $R^5$ is hydrogen, cyano, chloro, bromo, fluoro, methyl, or trifluoromethyl, most preferably cyano.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, cyano, halogen, methyl, halomethyl, methoxy or halomethoxy, most preferably cyano or trifluoromethyl.

Preferably k is 0 or 1.

In one group of compounds of formula IC —$B^1$—$B^2$—$B^3$— is —C=N—O—. In another group of compounds of formula IC —$B^1$—$B^2$—$B^3$— is —C=N—O— and $Y^1$ is CH, $Y^2$ is CH, $Y^3$ is CH.

In another group of compounds of formula IC —$B^1$—$B^2$—$B^3$— is —C=N—O—, $Y^1$ is CH, $Y^2$ is CH, $Y^3$ is CH and $R^1$ is $CF_3$.

In another group of compounds of formula IC —$B^1$—$B^2$—$B^3$— is —C=N—O—, $Y^1$ is CH, $Y^2$ is CH, $Y^3$ is CH, $R^1$ is $CF_3$ and $R^5$ is cyano.

In another group of compounds of formula IC —$B^1$—$B^2$—$B^3$— is —C=N—O—, $Y^1$ is CH, $Y^2$ is CH, $Y^3$ is CH, $R^1$ is $CF_3$, and k is 0 or k is 1 and Z is cyano or trifluoromethyl.

In another group of compounds of formula IC —$B^1$—$B^2$—$B^3$— is —C=N—O—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula IC —$B^1$—$B^2$—$B^3$— is —C=N—O—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IC —$B^1$—$B^2$—$B^3$— is —C=N—$CH_2$—.

In another group of compounds of formula IC —$B^1$—$B^2$—$B^3$— is —C=N—$CH_2$—, $Y^1$ is CH, $Y^2$ is CH, $Y^3$ is CH.

In another group of compounds of formula IC —$B^1$—$B^2$—$B^3$— is —C=N—$CH_2$—, $Y^1$ is CH, $Y^2$ is CH, $Y^3$ is CH and $R^1$ is $CF_3$.

In another group of compounds of formula IC —$B^1$—$B^2$—$B^3$— is —C=N—$CH_2$—, $Y^1$ is CH, $Y^2$ is CH, $Y^3$ is CH, $R^1$ is $CF_3$ and $R^5$ is cyano.

In another group of compounds of formula IC —$B^1$—$B^2$—$B^3$— is —C=N—$CH_2$—, $Y^1$ is CH, $Y^2$ is CH, $Y^3$ is CH, $R^1$ is $CF_3$, and k is 0 or k is 1 and Z is cyano or trifluoromethyl.

In another group of compounds of formula IC —$B^1$—$B^2$—$B^3$— is —C=N—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula IC —$B^1$—$B^2$—$B^3$— is —C=N—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IC —$B^1$—$B^2$—$B^3$— is —N—$CH_2$—$CH_2$—.

In another group of compounds of formula IC —$B^1$—$B^2$—$B^3$— is —N—$CH_2$—$CH_2$— and $Y^1$ is CH, $Y^2$ is CH, $Y^3$ is CH.

In another group of compounds of formula IC —$B^1$—$B^2$—$B^3$— is —N—$CH_2$—$CH_2$—, $Y^1$ is CH, $Y^2$ is CH, $Y^3$ is CH and $R^1$ is $CF_3$.

In another group of compounds of formula IC —$B^1$—$B^2$—$B^3$— is —N—$CH_2$—$CH_2$—, $Y^1$ is CH, $Y^2$ is CH, $Y^3$ is CH, $R^1$ is $CF_3$ and $R^5$ is cyano.

In another group of compounds of formula IC —$B^1$—$B^2$—$B^3$— is —N—$CH_2$—$CH_2$—, $Y^1$ is CH, $Y^2$ is CH, $Y^3$ is CH, $R^1$ is $CF_3$, and k is 0 or k is 1 and Z is cyano or trifluoromethyl.

In another group of compounds of formula IC —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula IC —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IC —$B^1$—$B^2$—$B^3$— is —C=C—O—.

In another group of compounds of formula IC —$B^1$—$B^2$—$B^3$— is —C=C—O— and $Y^1$ is CH, $Y^2$ is CH, $Y^3$ is CH.

In another group of compounds of formula IC —$B^1$—$B^2$—$B^3$— is —C=C—O—, $Y^1$ is CH, $Y^2$ is CH, $Y^3$ is CH and $R^1$ is $CF_3$.

In another group of compounds of formula IC —$B^1$—$B^2$—$B^3$— is —C=C—O—, $Y^1$ is CH, $Y^2$ is CH, $Y^3$ is CH, $R^1$ is $CF_3$ and $R^5$ is cyano.

In another group of compounds of formula IC —$B^1$—$B^2$—$B^3$— is —C=C—O—, $Y^1$ is CH, $Y^2$ is CH, $Y^3$ is CH, $R^1$ is $CF_3$, and k is 0 or k is 1 and Z is cyano or trifluoromethyl.

In another group of compounds of formula IC —$B^1$—$B^2$—$B^3$— is —C=C—O—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula IC —$B^1$—$B^2$—$B^3$— is —C=C—O—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In another group of compounds of formula IC $R^5$ is cyano, k is 0 or 1 and Z is cyano or trifluoromethyl.

In another group of compounds of formula IC $R^5$ is cyano, $R^1$ is $CF_3$, —$B^1$—$B^2$—$B^3$— is —C=N—O— or —C=N—$CH_2$—, $Y^1$, $Y^2$ and $Y^3$ are CH, and k is 0.

In one embodiment the compound of formula I is a compound of formula ID

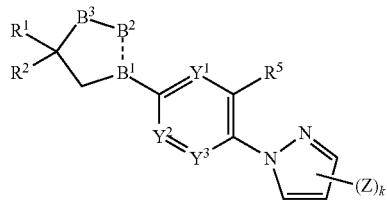

(ID)

wherein $B^1$, $B^2$, $B^3$, $R^1$, $R^2$, $Y^1$, $Y^2$, $Y^3$, $R^5$ Z and k are as defined for a compound of formula I In compounds of formula ID preferred definitions of $B^1$, $B^2$, $B^3$, $R^1$, $R^2$, $Y^1$, $Y^2$, $Y^3$, $R^5$ Z and k are, in any combination, as set out below Preferably $R^1$ is trifluoromethyl, or chlorodifluoromethyl, most preferably trifluoromethyl.

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl.

In one group of compounds $R^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, even more preferably $R^5$ is hydrogen, cyano, chloro, bromo, fluoro, methyl, or trifluoromethyl, most preferably cyano.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, cyano, halogen, methyl, halomethyl, methoxy or halomethoxy, most preferably cyano or trifluoromethyl.

Preferably k is 0 or 1.

In one group of compounds of formula ID —$B^1$—$B^2$—$B^3$— is —C=N—O—.

In another group of compounds of formula ID —$B^1$—$B^2$—$B^3$— is —C=N—O— and $Y^1$ is CH, $Y^2$ is CH, $Y^3$ is CH.

In another group of compounds of formula ID —$B^1$—$B^2$—$B^3$— is —C=N—O—, $Y^1$ is CH, $Y^2$ is CH, $Y^3$ is CH and $R^1$ is $CF_3$.

In another group of compounds of formula ID —$B^1$—$B^2$—$B^3$— is —C=N—O—, $Y^1$ is CH, $Y^2$ is CH, $Y^3$ is CH, $R^1$ is $CF_3$ and $R^5$ is cyano.

In another group of compounds of formula ID —$B^1$—$B^2$—$B^3$— is —C=N—O—, $Y^1$ is CH, $Y^2$ is CH, $Y^3$ is CH, $R^1$ is $CF_3$, and k is 0 or k is 1 and Z is cyano or trifluoromethyl.

In another group of compounds of formula ID —$B^1$—$B^2$—$B^3$— is —C=N—O—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula ID —$B^1$—$B^2$—$B^3$— is —C=N—O—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula ID —$B^1$—$B^2$—$B^3$— is —C=N—$CH_2$—.

In another group of compounds of formula ID —$B^1$—$B^2$—$B^3$— is —C=N—$CH_2$— and $Y^1$ is CH, $Y^2$ is CH, $Y^3$ is CH.

In another group of compounds of formula ID —$B^1$—$B^2$—$B^3$— is —C=N—$CH_2$—, $Y^1$ is CH, $Y^2$ is CH, $Y^3$ is CH and $R^1$ is $CF_3$.

In another group of compounds of formula ID —$B^1$—$B^2$—$B^3$— is —C=N—$CH_2$—, $Y^1$ is CH, $Y^2$ is CH, $Y^3$ is CH, $R^1$ is $CF_3$ and $R^5$ is cyano.

In another group of compounds of formula ID —$B^1$—$B^2$—$B^3$— is —C=N—$CH_2$—, $Y^1$ is CH, $Y^2$ is CH, $Y^3$ is CH, $R^1$ is $CF_3$, and k is 0 or k is 1 and Z is cyano or trifluoromethyl.

In another group of compounds of formula ID —$B^1$—$B^2$—$B^3$— is —C=N—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula ID —$B^1$—$B^2$—$B^3$— is —C=N—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula ID —$B^1$—$B^2$—$B^3$— is —N—$CH_2$—$CH_2$—.

In another group of compounds of formula ID —$B^1$—$B^2$—$B^3$— is —N—$CH_2$—$CH_2$— and $Y^1$ is CH, $Y^2$ is CH, $Y^3$ is CH.

In another group of compounds of formula ID —$B^1$—$B^2$—$B^3$— is —N—$CH_2$—$CH_2$—, $Y^1$ is CH, $Y^2$ is CH, $Y^3$ is CH and $R^1$ is $CF_3$.

In another group of compounds of formula ID —$B^1$—$B^2$—$B^3$— is —N—$CH_2$—$CH_2$—, $Y^1$ is CH, $Y^2$ is CH, $Y^3$ is CH, $R^1$ is $CF_3$ and $R^5$ is cyano.

In another group of compounds of formula ID —$B^1$—$B^2$—$B^3$— is —N—$CH_2$—$CH_2$—, $Y^1$ is CH, $Y^2$ is CH, $Y^3$ is CH, $R^1$ is $CF_3$, and k is 0 or k is 1 and Z is cyano or trifluoromethyl.

In another group of compounds of formula ID —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula ID —$B^1$—$B^2$—$B^3$— is —N—$CH_2$—$CH_2$—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl- In one group of compounds of formula ID —$B^1$—$B^2$—$B^3$— is —C=C—O—.

In another group of compounds of formula ID —$B^1$—$B^2$—$B^3$— is —C=C—O— and $Y^1$ is CH, $Y^2$ is CH, $Y^3$ is CH.

In another group of compounds of formula ID —$B^1$—$B^2$—$B^3$— is —C=C—O—, $Y^1$ is CH, $Y^2$ is CH, $Y^3$ is CH and $R^1$ is $CF_3$.

In another group of compounds of formula ID —$B^1$—$B^2$—$B^3$— is —C=C—O—, $Y^1$ is CH, $Y^2$ is CH, $Y^3$ is CH, $R^1$ is $CF_3$ and $R^5$ is cyano.

In another group of compounds of formula ID —$B^1$—$B^2$—$B^3$— is —C=C—O—, $Y^1$ is CH, $Y^2$ is CH, $Y^3$ is CH, $R^1$ is $CF_3$, and k is 0 or k is 1 and Z is cyano or trifluoromethyl.

In another group of compounds of formula ID —$B^1$—$B^2$—$B^3$— is —C=C—O—, $Y^1$ is CH, $Y^2$ is CH, $Y^3$ is CH, $R^1$ is $CF_3$, $R^5$ is cyano and k is 0 or k is 1 and Z is cyano or trifluoromethyl.

In another group of compounds of formula ID —$B^1$—$B^2$—$B^3$— is —C=C—O—, $Y^1$ is CH, $Y^2$ is CH, $Y^3$ is CH, $R^1$ is $CF_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In another group of compounds of formula D $R^5$ is cyano, k is 0 or 1 and Z is cyano or trifluoromethyl.

In another group of compounds of formula ID $R^5$ is cyano, k is 0 or 1 and Z is cyano or trifluoromethyl, $R^1$ is $CF_3$, —$B^1$—$B^2$—$B^3$— is —C=N—O— or —C=N—$CH_2$—, $Y^1$, $Y^2$ and $Y^3$ are CH.

The following compounds of formula I-1, I-2, I-3 and I-4 illustrate the compounds of formula I when —$B^1$—$B^2$—$B^3$— is —C=N—O—, —C=N—$CH_2$—, —N—$CH_2$—$CH_2$—, or —C=C—O— respectively.

(I-1)

(I-2)

(I-3)

(I-4)

Tables 1 to 36 below illustrate compounds of the invention.

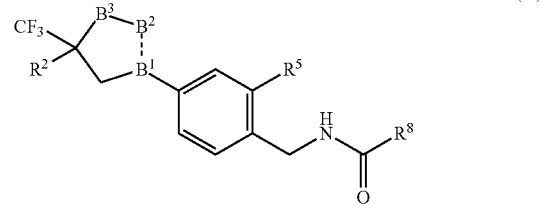

(Ia)

Table 1

Table 1 provides 288 compounds of formula Ia wherein R5 is hydrogen, B1-B2-B3 is C=N—O, and R2 and R8 are as defined in Table P.

Table 2

Table 2 provides 288 compounds of formula Ia wherein R5 is methyl, B1-B2-B3 is C=N—O, and R2 and R8 are as defined in Table P.

Table 3

Table 3 provides 288 compounds of formula Ia wherein R5 is trifluoromethyl, B1-B2-B3 is C=N—O, and R2 and R8 are as defined in Table P.

Table 4
Table 4 provides 288 compounds of formula Ia wherein R5 is chloro, B1-B2-B3 is C=N—O, and R2 and R8 are as defined in Table P.

Table 5
Table 5 provides 288 compounds of formula Ia wherein R5 is bromo, B1-B2-B3 is C=N—O, and R2 and R8 are as defined in Table P.

Table 6
Table 6 provides 288 compounds of formula Ia wherein R5 is hydrogen, B1-B2-B3 is C=N—CH2, and R2 and R8 are as defined in Table P.

Table 7
Table 7 provides 288 compounds of formula Ia wherein R5 is methyl, B1-B2-B3 is C=N—CH2, and R2 and R8 are as defined in Table P.

Table 8
Table 8 provides 288 compounds of formula Ia wherein R5 is trifluoromethyl, B1-B2-B3 is C=N—CH2, and R2 and R8 are as defined in Table P.

Table 9
Table 9 provides 288 compounds of formula Ia wherein R5 is chloro, B1-B2-B3 is C=N—CH2, and R2 and R8 are as defined in Table P.

Table 10
Table 10 provides 288 compounds of formula Ia wherein R5 is bromo, B1-B2-B3 is C=N—CH2, and R2 and R8 are as defined in Table P.

Table 11
Table 11 provides 288 compounds of formula Ia wherein R5 is hydrogen, B1-B2-B3 is N—CH2-CH2, and R2 and R8 are as defined in Table P.

Table 12
Table 12 provides 288 compounds of formula Ia wherein R5 is methyl, B1-B2-B3 is N—CH2-CH2, and R2 and R8 are as defined in Table P.

Table 13
Table 13 provides 288 compounds of formula Ia wherein R5 is trifluoromethyl, B1-B2-B3 is N—CH2-CH2, and R2 and R8 are as defined in Table P.

Table 14
Table 14 provides 288 compounds of formula Ia wherein R5 is chloro, B1-B2-B3 is N—CH2-CH2, and R2 and R8 are as defined in Table P.

Table 15
Table 15 provides 288 compounds of formula Ia wherein R5 is bromo, B1-B2-B3 is N—CH2-CH2, and R2 and R8 are as defined in Table P.

Table 16
Table 16 provides 288 compounds of formula Ia wherein R5 is hydrogen, B1-B2-B3 is C=C—O, and R2 and R8 are as defined in Table P.

Table 17
Table 17 provides 288 compounds of formula Ia wherein R5 is methyl, B1-B2-B3 is C=C—O, and R2 and R8 are as defined in Table P.

Table 18
Table 18 provides 288 compounds of formula Ia wherein R5 is trifluoromethyl, B1-B2-B3 is C=C—O, and R2 and R8 are as defined in Table P.

Table 19
Table 19 provides 288 compounds of formula Ia wherein R5 is chloro, B1-B2-B3 is C=C—O, and R2 and R8 are as defined in Table P.

Table 20
Table 20 provides 288 compounds of formula Ia wherein R5 is bromo, B1-B2-B3 is C=C—O, and R2 and R8 are as defined in Table P.

TABLE P

|    | R2 | R8 |
|----|----|----|
| 1  | 3,5-dichlorophenyl | methyl |
| 2  | 3-chloro-4-fluorophenyl | methyl |
| 3  | 3-fluoro-4-chlorophenyl | methyl |
| 4  | 3,4-dichlorophenyl | methyl |
| 5  | 3-chloro-4-bromophenyl | methyl |
| 6  | 3,5-dichloro-4-fluorophenyl | methyl |
| 7  | 3,4,5-trichlorophenyl | methyl |
| 8  | 3,5-dichloro-4-iodophenyl | methyl |
| 9  | 3,4,5-trifluorophenyl | methyl |
| 10 | 3-chloro-5-bromophenyl | methyl |
| 11 | 3-chloro-5-fluorophenyl | methyl |
| 12 | 3-chloro-5-(trifluoromethyl)phenyl | methyl |
| 13 | 3,4-dichloro-5-(trifluoromethyl)phenyl | methyl |
| 14 | 3,5-bis(trifluoromethyl)phenyl | methyl |
| 15 | 4-chloro-3,5-bis(trifluoromethyl)phenyl | methyl |
| 16 | 3-(trifluoromethyl)phenyl | methyl |
| 17 | 2,6-dichloro-4-pyridyl | methyl |
| 18 | 2,6-bis(trifluoromethyl)-4-pyridyl | methyl |
| 19 | 3,5-dichlorophenyl | ethyl |
| 20 | 3-chloro-4-fluorophenyl | ethyl |
| 21 | 3-fluoro-4-chlorophenyl | ethyl |
| 22 | 3,4-dichlorophenyl | ethyl |
| 23 | 3-chloro-4-bromophenyl | ethyl |
| 24 | 3,5-dichloro-4-fluorophenyl | ethyl |
| 25 | 3,4,5-trichlorophenyl | ethyl |
| 26 | 3,5-dichloro-4-iodophenyl | ethyl |
| 27 | 3,4,5-trifluorophenyl | ethyl |
| 28 | 3-chloro-5-bromophenyl | ethyl |
| 29 | 3-chloro-5-fluorophenyl | ethyl |
| 30 | 3-chloro-5-(trifluoromethyl)phenyl | ethyl |
| 31 | 3,4-dichloro-5-(trifluoromethyl)phenyl | ethyl |
| 32 | 3,5-bis(trifluoromethyl)phenyl | ethyl |
| 33 | 4-chloro-3,5-bis(trifluoromethyl)phenyl | ethyl |
| 34 | 3-(trifluoromethyl)phenyl | ethyl |
| 35 | 2,6-dichloro-4-pyridyl | ethyl |
| 36 | 2,6-bis(trifluoromethyl)-4-pyridyl | ethyl |
| 37 | 3,5-dichlorophenyl | propyl |
| 38 | 3-chloro-4-fluorophenyl | propyl |
| 39 | 3-fluoro-4-chlorophenyl | propyl |
| 40 | 3,4-dichlorophenyl | propyl |
| 41 | 3-chloro-4-bromophenyl | propyl |
| 42 | 3,5-dichloro-4-fluorophenyl | propyl |
| 43 | 3,4,5-trichlorophenyl | propyl |
| 44 | 3,5-dichloro-4-iodophenyl | propyl |
| 45 | 3,4,5-trifluorophenyl | propyl |
| 46 | 3-chloro-5-bromophenyl | propyl |
| 47 | 3-chloro-5-fluorophenyl | propyl |
| 48 | 3-chloro-5-(trifluoromethyl)phenyl | propyl |
| 49 | 3,4-dichloro-5-(trifluoromethyl)phenyl | propyl |
| 50 | 3,5-bis(trifluoromethyl)phenyl | propyl |
| 51 | 4-chloro-3,5-bis(trifluoromethyl)phenyl | propyl |
| 52 | 3-(trifluoromethyl)phenyl | propyl |
| 53 | 2,6-dichloro-4-pyridyl | propyl |
| 54 | 2,6-bis(trifluoromethyl)-4-pyridyl | propyl |
| 55 | 3,5-dichlorophenyl | isopropyl |
| 56 | 3-chloro-4-fluorophenyl | isopropyl |
| 57 | 3-fluoro-4-chlorophenyl | isopropyl |
| 58 | 3,4-dichlorophenyl | isopropyl |
| 59 | 3-chloro-4-bromophenyl | isopropyl |
| 60 | 3,5-dichloro-4-fluorophenyl | isopropyl |
| 61 | 3,4,5-trichlorophenyl | isopropyl |
| 62 | 3,5-dichloro-4-iodophenyl | isopropyl |
| 63 | 3,4,5-trifluorophenyl | isopropyl |
| 64 | 3-chloro-5-bromophenyl | isopropyl |
| 65 | 3-chloro-5-fluorophenyl | isopropyl |
| 66 | 3-chloro-5-(trifluoromethyl)phenyl | isopropyl |
| 67 | 3,4-dichloro-5-(trifluoromethyl)phenyl | isopropyl |
| 68 | 3,5-bis(trifluoromethyl)phenyl | isopropyl |
| 69 | 4-chloro-3,5-bis(trifluoromethyl)phenyl | isopropyl |
| 70 | 3-(trifluoromethyl)phenyl | isopropyl |
| 71 | 2,6-dichloro-4-pyridyl | isopropyl |
| 72 | 2,6-bis(trifluoromethyl)-4-pyridyl | isopropyl |

TABLE P-continued

| | R2 | R8 |
|---|---|---|
| 73 | 3,5-dichlorophenyl | CH3CH2CH(CH3)— |
| 74 | 3-chloro-4-fluorophenyl | CH3CH2CH(CH3)— |
| 75 | 3-fluoro-4-chlorophenyl | CH3CH2CH(CH3)— |
| 76 | 3,4-dichlorophenyl | CH3CH2CH(CH3)— |
| 77 | 3-chloro-4-bromophenyl | CH3CH2CH(CH3)— |
| 78 | 3,5-dichloro-4-fluorophenyl | CH3CH2CH(CH3)— |
| 79 | 3,4,5-trichlorophenyl | CH3CH2CH(CH3)— |
| 80 | 3,5-dichloro-4-iodophenyl | CH3CH2CH(CH3)— |
| 81 | 3,4,5-trifluorophenyl | CH3CH2CH(CH3)— |
| 82 | 3-chloro-5-bromophenyl | CH3CH2CH(CH3)— |
| 83 | 3-chloro-5-fluorophenyl | CH3CH2CH(CH3)— |
| 84 | 3-chloro-5-(trifluoromethyl)phenyl | CH3CH2CH(CH3)— |
| 85 | 3,4-dichloro-5-(trifluoromethyl)phenyl | CH3CH2CH(CH3)— |
| 86 | 3,5-bis(trifluoromethyl)phenyl | CH3CH2CH(CH3)— |
| 87 | 4-chloro-3,5-bis(trifluoromethyl)phenyl | CH3CH2CH(CH3)— |
| 88 | 3-(trifluoromethyl)phenyl | CH3CH2CH(CH3)— |
| 89 | 2,6-dichloro-4-pyridyl | CH3CH2CH(CH3)— |
| 90 | 2,6-bis(trifluoromethyl)-4-pyridyl | CH3CH2CH(CH3)— |
| 91 | 3,5-dichlorophenyl | CH3OCH2— |
| 92 | 3-chloro-4-fluorophenyl | CH3OCH2— |
| 93 | 3-fluoro-4-chlorophenyl | CH3OCH2— |
| 94 | 3,4-dichlorophenyl | CH3OCH2— |
| 95 | 3-chloro-4-bromophenyl | CH3OCH2— |
| 96 | 3,5-dichloro-4-fluorophenyl | CH3OCH2— |
| 97 | 3,4,5-trichlorophenyl | CH3OCH2— |
| 98 | 3,5-dichloro-4-iodophenyl | CH3OCH2— |
| 99 | 3,4,5-trifluorophenyl | CH3OCH2— |
| 100 | 3-chloro-5-bromophenyl | CH3OCH2— |
| 101 | 3-chloro-5-fluorophenyl | CH3OCH2— |
| 102 | 3-chloro-5-(trifluoromethyl)phenyl | CH3OCH2— |
| 103 | 3,4-dichloro-5-(trifluoromethyl)phenyl | CH3OCH2— |
| 104 | 3,5-bis(trifluoromethyl)phenyl | CH3OCH2— |
| 105 | 4-chloro-3,5-bis(trifluoromethyl)phenyl | CH3OCH2— |
| 106 | 3-(trifluoromethyl)phenyl | CH3OCH2— |
| 107 | 2,6-dichloro-4-pyridyl | CH3OCH2— |
| 108 | 2,6-bis(trifluoromethyl)-4-pyridyl | CH3OCH2— |
| 109 | 3,5-dichlorophenyl | CH3OCH2CH2— |
| 110 | 3-chloro-4-fluorophenyl | CH3OCH2CH2— |
| 111 | 3-fluoro-4-chlorophenyl | CH3OCH2CH2— |
| 112 | 3,4-dichlorophenyl | CH3OCH2CH2— |
| 113 | 3-chloro-4-bromophenyl | CH3OCH2CH2— |
| 114 | 3,5-dichloro-4-fluorophenyl | CH3OCH2CH2— |
| 115 | 3,4,5-trichlorophenyl | CH3OCH2CH2— |
| 116 | 3,5-dichloro-4-iodophenyl | CH3OCH2CH2— |
| 117 | 3,4,5-trifluorophenyl | CH3OCH2CH2— |
| 118 | 3-chloro-5-bromophenyl | CH3OCH2CH2— |
| 119 | 3-chloro-5-fluorophenyl | CH3OCH2CH2— |
| 120 | 3-chloro-5-(trifluoromethyl)phenyl | CH3OCH2CH2— |
| 121 | 3,4-dichloro-5-(trifluoromethyl)phenyl | CH3OCH2CH2— |
| 122 | 3,5-bis(trifluoromethyl)phenyl | CH3OCH2CH2— |
| 123 | 4-chloro-3,5-bis(trifluoromethyl)phenyl | CH3OCH2CH2— |
| 124 | 3-(trifluoromethyl)phenyl | CH3OCH2CH2— |
| 125 | 2,6-dichloro-4-pyridyl | CH3OCH2CH2— |
| 126 | 2,6-bis(trifluoromethyl)-4-pyridyl | CH3OCH2CH2— |
| 127 | 3,5-dichlorophenyl | CH3OCH(CH3)CH2— |
| 128 | 3-chloro-4-fluorophenyl | CH3OCH(CH3)CH2— |
| 129 | 3-fluoro-4-chlorophenyl | CH3OCH(CH3)CH2— |
| 130 | 3,4-dichlorophenyl | CH3OCH(CH3)CH2— |
| 131 | 3-chloro-4-bromophenyl | CH3OCH(CH3)CH2— |
| 132 | 3,5-dichloro-4-fluorophenyl | CH3OCH(CH3)CH2— |
| 133 | 3,4,5-trichlorophenyl | CH3OCH(CH3)CH2— |
| 134 | 3,5-dichloro-4-iodophenyl | CH3OCH(CH3)CH2— |
| 135 | 3,4,5-trifluorophenyl | CH3OCH(CH3)CH2— |
| 136 | 3-chloro-5-bromophenyl | CH3OCH(CH3)CH2— |
| 137 | 3-chloro-5-fluorophenyl | CH3OCH(CH3)CH2— |
| 138 | 3-chloro-5-(trifluoromethyl)phenyl | CH3OCH(CH3)CH2— |
| 139 | 3,4-dichloro-5-(trifluoromethyl)phenyl | CH3OCH(CH3)CH2— |
| 140 | 3,5-bis(trifluoromethyl)phenyl | CH3OCH(CH3)CH2— |
| 141 | 4-chloro-3,5-bis(trifluoromethyl)phenyl | CH3OCH(CH3)CH2— |
| 142 | 3-(trifluoromethyl)phenyl | CH3OCH(CH3)CH2— |
| 143 | 2,6-dichloro-4-pyridyl | CH3OCH(CH3)CH2— |
| 144 | 2,6-bis(trifluoromethyl)-4-pyridyl | CH3OCH(CH3)CH2— |
| 145 | 3,5-dichlorophenyl | cyclopropyl |
| 146 | 3-chloro-4-fluorophenyl | cyclopropyl |
| 147 | 3-fluoro-4-chlorophenyl | cyclopropyl |
| 148 | 3,4-dichlorophenyl | cyclopropyl |
| 149 | 3-chloro-4-bromophenyl | cyclopropyl |
| 150 | 3,5-dichloro-4-fluorophenyl | cyclopropyl |
| 151 | 3,4,5-trichlorophenyl | cyclopropyl |
| 152 | 3,5-dichloro-4-iodophenyl | cyclopropyl |
| 153 | 3,4,5-trifluorophenyl | cyclopropyl |
| 154 | 3-chloro-5-bromophenyl | cyclopropyl |
| 155 | 3-chloro-5-fluorophenyl | cyclopropyl |
| 156 | 3-chloro-5-(trifluoromethyl)phenyl | cyclopropyl |
| 157 | 3,4-dichloro-5-(trifluoromethyl)phenyl | cyclopropyl |
| 158 | 3,5-bis(trifluoromethyl)phenyl | cyclopropyl |
| 159 | 4-chloro-3,5-bis(trifluoromethyl)phenyl | cyclopropyl |
| 160 | 3-(trifluoromethyl)phenyl | cyclopropyl |
| 161 | 2,6-dichloro-4-pyridyl | cyclopropyl |
| 162 | 2,6-bis(trifluoromethyl)-4-pyridyl | cyclopropyl |
| 163 | 3,5-dichlorophenyl | Cyclopropyl-CH2— |
| 164 | 3-chloro-4-fluorophenyl | Cyclopropyl-CH2— |
| 165 | 3-fluoro-4-chlorophenyl | Cyclopropyl-CH2— |
| 166 | 3,4-dichlorophenyl | Cyclopropyl-CH2— |
| 167 | 3-chloro-4-bromophenyl | Cyclopropyl-CH2— |
| 168 | 3,5-dichloro-4-fluorophenyl | Cyclopropyl-CH2— |
| 169 | 3,4,5-trichlorophenyl | Cyclopropyl-CH2— |
| 170 | 3,5-dichloro-4-iodophenyl | Cyclopropyl-CH2— |
| 171 | 3,4,5-trifluorophenyl | Cyclopropyl-CH2— |
| 172 | 3-chloro-5-bromophenyl | Cyclopropyl-CH2— |
| 173 | 3-chloro-5-fluorophenyl | Cyclopropyl-CH2— |
| 174 | 3-chloro-5-(trifluoromethyl)phenyl | Cyclopropyl-CH2— |
| 175 | 3,4-dichloro-5-(trifluoromethyl)phenyl | Cyclopropyl-CH2— |
| 176 | 3,5-bis(trifluoromethyl)phenyl | Cyclopropyl-CH2— |
| 177 | 4-chloro-3,5-bis(trifluoromethyl)phenyl | Cyclopropyl-CH2— |
| 178 | 3-(trifluoromethyl)phenyl | Cyclopropyl-CH2— |
| 179 | 2,6-dichloro-4-pyridyl | Cyclopropyl-CH2— |
| 180 | 2,6-bis(trifluoromethyl)-4-pyridyl | Cyclopropyl-CH2— |
| 181 | 3,5-dichlorophenyl | cyclobutyl |
| 182 | 3-chloro-4-fluorophenyl | cyclobutyl |
| 183 | 3-fluoro-4-chlorophenyl | cyclobutyl |
| 184 | 3,4-dichlorophenyl | cyclobutyl |
| 185 | 3-chloro-4-bromophenyl | cyclobutyl |
| 186 | 3,5-dichloro-4-fluorophenyl | cyclobutyl |
| 187 | 3,4,5-trichlorophenyl | cyclobutyl |
| 188 | 3,5-dichloro-4-iodophenyl | cyclobutyl |
| 189 | 3,4,5-trifluorophenyl | cyclobutyl |
| 190 | 3-chloro-5-bromophenyl | cyclobutyl |
| 191 | 3-chloro-5-fluorophenyl | cyclobutyl |
| 192 | 3-chloro-5-(trifluoromethyl)phenyl | cyclobutyl |
| 193 | 3,4-dichloro-5-(trifluoromethyl)phenyl | cyclobutyl |
| 194 | 3,5-bis(trifluoromethyl)phenyl | cyclobutyl |
| 195 | 4-chloro-3,5-bis(trifluoromethyl)phenyl | cyclobutyl |
| 196 | 3-(trifluoromethyl)phenyl | cyclobutyl |
| 197 | 2,6-dichloro-4-pyridyl | cyclobutyl |
| 198 | 2,6-bis(trifluoromethyl)-4-pyridyl | cyclobutyl |
| 199 | 3,5-dichlorophenyl | CH3—S—CH2— |
| 200 | 3-chloro-4-fluorophenyl | CH3—S—CH2— |
| 201 | 3-fluoro-4-chlorophenyl | CH3—S—CH2— |
| 202 | 3,4-dichlorophenyl | CH3—S—CH2— |
| 203 | 3-chloro-4-bromophenyl | CH3—S—CH2— |
| 204 | 3,5-dichloro-4-fluorophenyl | CH3—S—CH2— |
| 205 | 3,4,5-trichlorophenyl | CH3—S—CH2— |
| 206 | 3,5-dichloro-4-iodophenyl | CH3—S—CH2— |
| 207 | 3,4,5-trifluorophenyl | CH3—S—CH2— |
| 208 | 3-chloro-5-bromophenyl | CH3—S—CH2— |
| 209 | 3-chloro-5-fluorophenyl | CH3—S—CH2— |
| 210 | 3-chloro-5-(trifluoromethyl)phenyl | CH3—S—CH2— |
| 211 | 3,4-dichloro-5-(trifluoromethyl)phenyl | CH3—S—CH2— |
| 212 | 3,5-bis(trifluoromethyl)phenyl | CH3—S—CH2— |
| 213 | 4-chloro-3,5-bis(trifluoromethyl)phenyl | CH3—S—CH2— |
| 214 | 3-(trifluoromethyl)phenyl | CH3—S—CH2— |
| 215 | 2,6-dichloro-4-pyridyl | CH3—S—CH2— |
| 216 | 2,6-bis(trifluoromethyl)-4-pyridyl | CH3—S—CH2— |
| 217 | 3,5-dichlorophenyl | CH3—S(O)—CH2— |
| 218 | 3-chloro-4-fluorophenyl | CH3—S(O)—CH2— |
| 219 | 3-fluoro-4-chlorophenyl | CH3—S(O)—CH2— |
| 220 | 3,4-dichlorophenyl | CH3—S(O)—CH2— |
| 221 | 3-chloro-4-bromophenyl | CH3—S(O)—CH2— |
| 222 | 3,5-dichloro-4-fluorophenyl | CH3—S(O)—CH2— |
| 223 | 3,4,5-trichlorophenyl | CH3—S(O)—CH2— |
| 224 | 3,5-dichloro-4-iodophenyl | CH3—S(O)—CH2— |
| 225 | 3,4,5-trifluorophenyl | CH3—S(O)—CH2— |
| 226 | 3-chloro-5-bromophenyl | CH3—S(O)—CH2— |
| 227 | 3-chloro-5-fluorophenyl | CH3—S(O)—CH2— |
| 228 | 3-chloro-5-(trifluoromethyl)phenyl | CH3—S(O)—CH2— |

TABLE P-continued

| | R2 | R8 |
|---|---|---|
| 229 | 3,4-dichloro-5-(trifluoromethyl)phenyl | CH3—S(O)—CH2— |
| 230 | 3,5-bis(trifluoromethyl)phenyl | CH3—S(O)—CH2— |
| 231 | 4-chloro-3,5-bis(trifluoromethyl)phenyl | CH3—S(O)—CH2— |
| 232 | 3-(trifluoromethyl)phenyl | CH3—S(O)—CH2— |
| 233 | 2,6-dichloro-4-pyridyl | CH3—S(O)—CH2— |
| 234 | 2,6-bis(trifluoromethyl)-4-pyridyl | CH3—S(O)—CH2— |
| 235 | 3,5-dichlorophenyl | CH3—S(O2)—CH2— |
| 236 | 3-chloro-4-fluorophenyl | CH3—S(O2)—CH2— |
| 237 | 3-fluoro-4-chlorophenyl | CH3—S(O2)—CH2— |
| 238 | 3,4-dichlorophenyl | CH3—S(O2)—CH2— |
| 239 | 3-chloro-4-bromophenyl | CH3—S(O2)—CH2— |
| 240 | 3,5-dichloro-4-fluorophenyl | CH3—S(O2)—CH2— |
| 241 | 3,4,5-trichlorophenyl | CH3—S(O2)—CH2— |
| 242 | 3,5-dichloro-4-iodophenyl | CH3—S(O2)—CH2— |
| 243 | 3,4,5-trifluorophenyl | CH3—S(O2)—CH2— |
| 244 | 3-chloro-5-bromophenyl | CH3—S(O2)—CH2— |
| 245 | 3-chloro-5-fluorophenyl | CH3—S(O2)—CH2— |
| 246 | 3-chloro-5-(trifluoromethyl)phenyl | CH3—S(O2)—CH2— |
| 247 | 3,4-dichloro-5-(trifluoromethyl)phenyl | CH3—S(O2)—CH2— |
| 248 | 3,5-bis(trifluoromethyl)phenyl | CH3—S(O2)—CH2— |
| 249 | 4-chloro-3,5-bis(trifluoromethyl)phenyl | CH3—S(O2)—CH2— |
| 250 | 3-(trifluoromethyl)phenyl | CH3—S(O2)—CH2— |
| 251 | 2,6-dichloro-4-pyridyl | CH3—S(O2)—CH2— |
| 252 | 2,6-bis(trifluoromethyl)-4-pyridyl | CH3—S(O2)—CH2— |
| 253 | 3,5-dichlorophenyl | tetrahydrofuran-2-yl |
| 254 | 3-chloro-4-fluorophenyl | tetrahydrofuran-2-yl |
| 255 | 3-fluoro-4-chlorophenyl | tetrahydrofuran-2-yl |
| 256 | 3,4-dichlorophenyl | tetrahydrofuran-2-yl |
| 257 | 3-chloro-4-bromophenyl | tetrahydrofuran-2-yl |
| 258 | 3,5-dichloro-4-fluorophenyl | tetrahydrofuran-2-yl |
| 259 | 3,4,5-trichlorophenyl | tetrahydrofuran-2-yl |
| 260 | 3,5-dichloro-4-iodophenyl | tetrahydrofuran-2-yl |
| 261 | 3,4,5-trifluorophenyl | tetrahydrofuran-2-yl |
| 262 | 3-chloro-5-bromophenyl | tetrahydrofuran-2-yl |
| 263 | 3-chloro-5-fluorophenyl | tetrahydrofuran-2-yl |
| 264 | 3-chloro-5-(trifluoromethyl)phenyl | tetrahydrofuran-2-yl |
| 265 | 3,4-dichloro-5-(trifluoromethyl)phenyl | tetrahydrofuran-2-yl |
| 266 | 3,5-bis(trifluoromethyl)phenyl | tetrahydrofuran-2-yl |
| 267 | 4-chloro-3,5-bis(trifluoromethyl)phenyl | tetrahydrofuran-2-yl |
| 268 | 3-(trifluoromethyl)phenyl | tetrahydrofuran-2-yl |
| 269 | 2,6-dichloro-4-pyridyl | tetrahydrofuran-2-yl |
| 270 | 2,6-bis(trifluoromethyl)-4-pyridyl | tetrahydrofuran-2-yl |
| 271 | 3,5-dichlorophenyl | tetrahydrofuran-3-yl |
| 272 | 3-chloro-4-fluorophenyl | tetrahydrofuran-3-yl |
| 273 | 3-fluoro-4-chlorophenyl | tetrahydrofuran-3-yl |
| 274 | 3,4-dichlorophenyl | tetrahydrofuran-3-yl |
| 275 | 3-chloro-4-bromophenyl | tetrahydrofuran-3-yl |
| 276 | 3,5-dichloro-4-fluorophenyl | tetrahydrofuran-3-yl |
| 277 | 3,4,5-trichlorophenyl | tetrahydrofuran-3-yl |
| 278 | 3,5-dichloro-4-iodophenyl | tetrahydrofuran-3-yl |
| 279 | 3,4,5-trifluorophenyl | tetrahydrofuran-3-yl |
| 280 | 3-chloro-5-bromophenyl | tetrahydrofuran-3-yl |
| 281 | 3-chloro-5-fluorophenyl | tetrahydrofuran-3-yl |
| 282 | 3-chloro-5-(trifluoromethyl)phenyl | tetrahydrofuran-3-yl |
| 283 | 3,4-dichloro-5-(trifluoromethyl)phenyl | tetrahydrofuran-3-yl |
| 284 | 3,5-bis(trifluoromethyl)phenyl | tetrahydrofuran-3-yl |
| 285 | 4-chloro-3,5-bis(trifluoromethyl)phenyl | tetrahydrofuran-3-yl |
| 286 | 3-(trifluoromethyl)phenyl | tetrahydrofuran-3-yl |
| 287 | 2,6-dichloro-4-pyridyl | tetrahydrofuran-3-yl |
| 288 | 2,6-bis(trifluoromethyl)-4-pyridyl | tetrahydrofuran-3-yl |

(Ib)

Table 21

Table 21 provides 288 compounds of formula Ib wherein B1-B2-B3 is C=N—O, and R2 and R8 are as defined in Table P.

Table 22

Table 22 provides 288 compounds of formula Ib wherein B1-B2-B3 is C=N—CH2, and R2 and R8 are as defined in Table P.

Table 23

Table 23 provides 288 compounds of formula Ib wherein B1-B2-B3 is N—CH2-CH2, and R2 and R8 are as defined in Table P.

Table 24

Table 24 provides 288 compounds of formula Ib wherein B1-B2-B3 is C=C—O, and R2 and R8 are as defined in Table P.

(Ic)

Table 25

Table 25 provides 18 compounds of formula Ic wherein B1-B2-B3 is C=N—O, and R2 is as defined in Table Q.

Table 26

Table 26 provides 18 compounds of formula Ic wherein B1-B2-B3 is C=N—CH2, and R2 is as defined in Table Q.

Table 27

Table 27 provides 18 compounds of formula Ic wherein B1-B2-B3 is N—CH2-CH2, and R2 is as defined in Table Q.

Table 28

Table 28 provides 18 compounds of formula Ic wherein B1-B2-B3 is C=C—O, and R2 is as defined in Table Q.

(Id)

Table 29

Table 29 provides 18 compounds of formula Id wherein k is CN, B1-B2-B3 is C=N—O and R2 is as defined in Table Q.

Table 30

Table 30 provides 18 compounds of formula Id wherein k is CF3, B1-B2-B3 is C=N—O and R2 is as defined in Table Q.

Table 31

Table 31 provides 18 compounds of formula Id wherein k is CN, B1-B2-B3 is C=N—CH2 and R2 is as defined in Table Q.

Table 32
Table 32 provides 18 compounds of formula Id wherein k is CF3, B1-B2-B3 is C=N—CH2 and R2 is as defined in Table Q.
Table 33
Table 33 provides 18 compounds of formula Id wherein k is CN, B1-B2-B3 is N—CH2-CH2 and R2 is as defined in Table Q.
Table 34
Table 34 provides 18 compounds of formula Id wherein k is CF3, B1-B2-B3 is N—CH2-CH2 and R2 is as defined in Table Q.
Table 35
Table 35 provides 18 compounds of formula Id wherein k is CN, B1-B2-B3 is C=C—O and R2 is as defined in Table Q.
Table 36
Table 36 provides 18 compounds of formula Id wherein k is CF3, B1-B2-B3 is C=C—O and R2 is as defined in Table Q.

TABLE Q

| | R2 |
|---|---|
| 1 | 3,5-dichlorophenyl |
| 2 | 3-chloro-4-fluorophenyl |
| 3 | 3-fluoro-4-chlorophenyl |
| 4 | 3,4-dichlorophenyl |
| 5 | 3-chloro-4-bromophenyl |
| 6 | 3,5-dichloro-4-fluorophenyl |
| 7 | 3,4,5-trichlorophenyl |
| 8 | 3,5-dichloro-4-iodophenyl |
| 9 | 3,4,5-trifluorophenyl |
| 10 | 3-chloro-5-bromophenyl |
| 11 | 3-chloro-5-fluorophenyl |
| 12 | 3-chloro-5-(trifluoromethyl)phenyl |
| 13 | 3,4-dichloro-5-(trifluoromethyl)phenyl |
| 14 | 3,5-bis(trifluoromethyl)phenyl |
| 15 | 4-chloro-3,5-bis(trifluoromethyl)phenyl |
| 16 | 3-(trifluoromethyl)phenyl |
| 17 | 2,6-dichloro-4-pyridyl |
| 18 | 2,6-bis(trifluoromethyl)-4-pyridyl |

Of compounds of formula Ia, compounds in Tables 2, 4, 7 and 9 are particularly preferred. Of compounds of formula Ib, compounds in Tables 21, 22 and 23 are particularly preferred. Of compounds of formula Ic, compounds in Tables 25 and 26 are particularly preferred. Of compounds of formula Id, compounds in Tables 29, 30, 31, and 32 are particularly preferred.

Of particular interest are compounds 25.1, 25.7, 26.1 and 26.7.

Compounds of formula I include at least one chiral centre and may exist as compounds of formula I* or compounds of formula I**. Compounds I* and I** are enantiomers if there is no other chiral center or epimers otherwise.

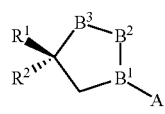
(I*)

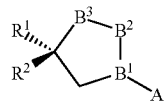
(I**)

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixtures of formula I*, the molar proportion of the compound of formula I* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound disclosed in Tables 1 to 36 represents a disclosure of a compound according to the compound of formula I* and a compound according to the compound of formula I**.

Likewise, group A2 may be group A2* or A2**.

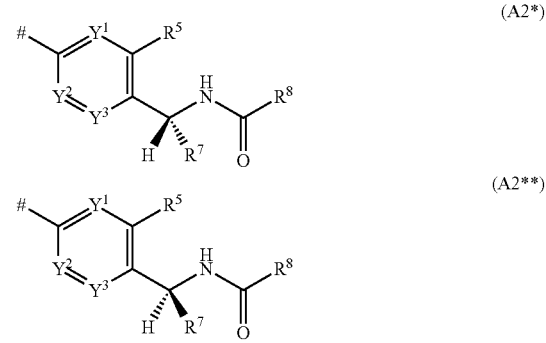

The invention includes mixtures of compounds of formula I with A2 as A2* and A2** in any ratio e.g. in a molar ratio of 1:99 to 99:1, e.g. 10:1 to 1:10, e.g. a substantially 50:50 molar ratio. In an enantiomerically (or epimerically) enriched mixture of formula I with A2 as A2*, the molar proportion of formula I with A2 as A2* compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula I with A2 as A2, the molar proportion of the compound of formula I with A2 as A2, compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I with A2 as A2** are preferred.

Each compound disclosed in Tables 21 to 24 represents a disclosure of I with A2 as A2* and a compound I with A2 as A2**. Each compound disclosed in Tables 21 to 24 represents a disclosure of a compound according to formula I* with A2 as A2*. Each compound disclosed in Tables 21 to 24 represents a disclosure of a compound according to formula I** with A2 as A2*. Each compound disclosed in Tables 21 to 24 represents a disclosure of a compound according to formula I* with A2 as A2. Each compound disclosed in Tables 21 to 24 represents a disclosure of a compound according to formula I with A2 as A2. Enantiomerically (or epimerically) enriched mixtures of formula I with A2 as A2** are preferred.

Reference to compounds of the invention also includes reference to salts and N-oxides.

The compounds of formula I may be prepared as described in WO08128711, WO10043315, WO11051455, WO07105814, WO08122375, WO09035004, WO09045999, WO09072621, WO09097992, WO10133336, WO10043315, WO11051455, WO11080211, JP2010235590, JP2011037817, JP2011178724, CN102210317, CN102246777, WO0907261, WO09097992, WO09051956.

The methods and uses of the invention are preferably for controlling and/or preventing infestation of the soybean crop by stink bugs, including stink bugs that are resistant to other insecticides, e.g. pyrethroid insecticides. Stinkbugs that are "resistant" to a particular insecticide refers e.g. to strains of stinkbugs that are less sensitive to that insecticide compared to the expected sensitivity of the same species of stinkbug. The expected sensitivity can be measured using e.g. a strain that has not previously been exposed to the insecticide.

Application is of the compounds of the invention is preferably to a crop of soybean plants, the locus thereof or propagation material thereof. Preferably application is to a crop of soybean plants or the locus thereof, more preferably to a crop of soybean plants. Application may be before infestation or when the pest is present. Application of the compounds of the invention can be performed according to any of the usual modes of application, e.g. foliar, drench, soil, in furrow etc. However, control of stinkbugs is usually achieved by foliar application, which is the preferred mode of application according to the invention.

The compounds of the invention may be applied in combination with an attractant. An attractant is a chemical that causes the insect to migrate towards the location of application. For control of stinkbugs it can be advantageous to apply the compounds of the invention with an attractant, particularly when the application is foliar. Stinkbugs are often located near to the ground, and application of an attractant may encourage migration up the plant towards the active ingredient. Suitable attractants include glucose, sacchrose, salt, glutamate (e.g. Aji-no-moto™), citric acid (e.g. Orobor™), soybean oil, peanut oil and soybean milk. Glutamate and citric acid are of particular interest, with citric acid being preferred.

An attractant may be premixed with the compound of the invention prior to application, e.g. as a readymix or tankmix, or by simultaneous application or sequential application to the plant. Suitable rates of attractants are for example 0.02 kg/ha-3 kg/ha.

The compounds of the invention are preferably used for pest control on soybean at 1:500 g/ha, preferably 10-70 g/ha.

The compounds of the invention are suitable for use on any soybean plant, including those that have been genetically modified to be resistant to active ingredients such as herbicides, or to produce biologically active compounds that control infestation by plant pests.

In a further preferred embodiment, transgenic plants and plant cultivars obtained by genetic engineering methods, if appropriate in combination with conventional methods (Genetically Modified Organisms), and parts thereof, are treated. Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques.

These can be cultivars, bio- or genotypes. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Traits that are emphasized in particular are the increased defence of the plants against insects, arachnids, nematodes and slugs and snails by virtue of toxins formed in the plants, in particular those formed in the plants by the genetic material from Bacillus thuringiensis (for example by the genes CrylA(a), CrylA(b), CrylA(c), CryllA, CryllA, CryIIIB2, Cry9c, Cry2Ab, Cry3Bb and CrylF and also combinations thereof) (referred to herein as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins.

Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants.

Examples of "Bt plants" are soya bean varieties which are sold under the trade names YIELD GARD®

Examples of herbicide-tolerant plants which may be mentioned are soybean varieties which are sold under the trade names Roundup Ready® (tolerance to glyphosate), Liberty Link® (tolerance to phosphinotricin), IMI® (tolerance to imidazolinones) and STS® (tolerance to sulphonylureas).

Herbicide-resistant plants (plants bred in a conventional manner for herbicide tolerance) which may be mentioned include the varieties sold under the name Clearfield® (for example maize).

Of particular interest are soybean plants carrying trains conferring resistance to 2.4D (e.g. Enlist®), glyphosate (e.g.

Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto). Soybean Cyst Nematode resistance soybean (SCN®-Syngenta) and soybean with Aphid resistant trait (AMT®-Syngneta) are also of interest.

These statements also apply to plant cultivars having these genetic traits or genetic traits still to be developed, which plant cultivars will be developed and/or marketed in the future.

The compounds of the invention may be used on soybean to control, for example, *Elasmopalpus lignosellus, Diloboderus abderus, Diabrotica speciosa, Sternechus subsignatus, Formicidae, Agrotis ypsilon, Julus* ssp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euchistus heros, stalk borer, Scaptocoris castanea, phyllophaga* spp., *Pseudoplusia includens, Spodoptera* spp., *Bemisia tabaci, Agriotes* spp., preferably *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* spp.

The compounds of the invention are preferably used on soybean to control stinkbugs, e.g. *Nezara* spp. (e.g. *Nezara viridula, Nezara antennata, Nezara hilare*), *Piezodorus* spp. (e.g. *Piezodorus guildinii*), *Acrosternum* spp. *Euchistus* spp. (e.g. *Euchistus heros, Euschistus servus*), *Halyomorpha halys, Plautia crossota, Riptortus clavatus, Rhopalus msculatus, Antestiopsis orbitalus, Dichelops* spp. (e.g. *Dichelops furcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euchistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros*. The compounds of the invention are particularly effective against *Euschistus* and in particular *Euchistus heros. Euschistus* and in particular *Euchistus heros* are the preferred targets.

In order to apply a compounds of the invention as an insecticide, acaricide, nematicide or molluscicide to a pest, a locus of pest, or to a plant susceptible to attack by a pest, compounds of the invention is usually formulated into a composition which includes, in addition to the compound of the invention, a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of the invention. The composition is generally used for the control of pests such that a compound of the invention is applied at a rate of from 0.1 g to 10 kg per hectare, preferably from 1 g to 6 kg per hectare, more preferably from 1 g to 1 kg per hectare.

When used in a seed dressing, a compound of the invention is used at a rate of 0.0001 g to 10 g (for example 0.001 g or 0.05 g), preferably 0.005 g to 10 g, more preferably 0.005 g to 4 g, per kilogram of seed.

Compositions comprising a compound of the invention can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of the invention.

Dustable powders (DP) may be prepared by mixing a compound of the invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of the invention with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the invention and one or more powdered solid diluents or carriers, or from pre-formed blank granules by absorbing a compound of the invention (or a solution thereof, in a suitable agent) in a porous granular material (such as pumice, attapulgite clays, fuller's earth, kieselguhr, diatomaceous earths or ground corn cobs) or by adsorbing a compound of the invention (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the invention in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of the invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the invention. SCs may be prepared by ball or bead milling the solid compound of the invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the invention may be dry milled and added to water, containing agents hereinbefore described, to produce the desired end product.

Aerosol formulations comprise a compound of the invention and a suitable propellant (for example n-butane). A compound of the invention may also be dissolved or dispersed in a suitable medium (for example water or a water miscible liquid, such as n-propanol) to provide compositions for use in non-pressurized, hand-actuated spray pumps.

A compound of the invention may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of the invention and, optionally, a carrier or diluent therefor. The polymeric shell may be produced by either an interfacial polycondensation reaction or by a coacervation procedure. The compositions may provide for controlled release of the compound of the invention and they may be used for seed treatment. A compound of the invention may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of the invention). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of the invention).

A compound of the invention may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of the invention may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of the invention may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of the invention (for example 0.0001 to 10%, by weight) depending upon the purpose for which they are to be used.

A compound of the invention may be used in mixtures with fertilizers (for example nitrogen-, potassium- or phosphorus-containing fertilizers). Suitable formulation types include granules of fertilizer. The mixtures preferably contain up to 25% by weight of the compound of the invention.

The invention therefore also provides a fertilizer composition comprising a fertilizer and a compound of the invention.

The compositions of this invention may contain other compounds having biological activity, for example micronutrients or compounds having fungicidal activity or which possess plant growth regulating, herbicidal, insecticidal, nematicidal or acaricidal activity.

The compound of the invention may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of the invention; or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;

f) Pyrazoles, such as tebufenpyrad, tolfenpyrad, ethiprole, pyriprole, fipronil, and fenpyroximate;

g) Macrolides, such as avermectins or milbemycins, for example abamectin, emamectin benzoate, ivermectin, milbemycin, spinosad, azadirachtin, milbemectin, lepimectin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, or nithiazine;

m) Diacylhydrazines, such as tebufenozide, chromafenozide or methoxyfenozide;

n) Diphenyl ethers, such as diofenolan or pyriproxifen;

o) Pyrazolines such as Indoxacarb or metaflumizone;

p) Ketoenols, such as Spirotetramat, spirodiclofen or spiromesifen;

q) Diamides, such as flubendiamide, chlorantraniliprole (Rynaxypyr®) or cyantraniliprole;

r) Essential oils such as Bugoil®-(PlantImpact); or s) a comopund selected from buprofezine, flonicamid, acequinocyl, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloro-pyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb, ziram; N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]amide.

Preferred additional pesticidally active ingredients are those selected from neonicotinoids, pyrethroids, strobilurins, triazoles and carboxamides (SDHI inhibitors). Pyrethroids are of interest of which lambda-cyhalothrin is of particular interest. Combinations of compounds of the invention and pyrethroids, in parrticular lambda-cyhalothrin, exhibit synergistic control of stinkbugs (according to the Colby formula), in particular *Euschistus*, e.g. *Euschistus heros*.

In a further aspect of the invention there is provided a method comprising applying to a crop of soybean plants, the locus thereof, or propagation material thereof, a combination of a compound a compound of the invention and lambda cyhalothrin in a synergistically effective amount, wherein the method is for control and/or prevention of stinkbugs, preferably *Euschistus*, e.g. *Euschistus heros*.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

Unless otherwise stated the weight ratio of the compound of I with an additional active ingredient may generally be between 1000:1 and 1:1000. In other embodiments that weight ratio of A to B may be between 500:1 to 1:500, for example between 100:1 to 1:100, for example between 1:50 to 50:1, for example 1:20 to 20:1, for example 1:10 to 10:1, for example 1:5 to 5:1, for example 1:1.

Compositions of the invention include those prepared by premixing prior to application, e.g. as a readymix or tank-mix, or by simultaneous application or sequential application to the plant.

The invention will now be illustrated by the following non-limiting Examples. All citations are incorporated by reference.

EXAMPLE 1

Preparation of N-[(1S)-1-[4-[3-[3,5-bis(trifluoromethyl)phenyl]-3-(trifluoromethyl)pyrrolidin-1-yl]phenyl]ethyl]cyclopropanecarboxamide

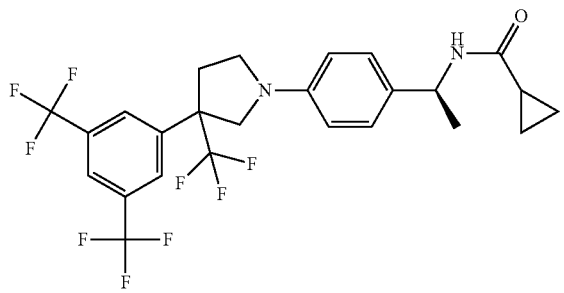 [SMILES: C[C@H](NC(=O)C1CC1)c1ccc(N2CCC(c3cc(C(F)(F)F)cc(C(F)(F)F)c3)(C(F)(F)F)C2)cc1]

To a solution of 3-[3,5-bis(trifluoromethyl)phenyl]-3-(trifluoromethyl)pyrrolidine (0.15 g, 0.4271 mmol, prepared as described in WO08128711) and N-[(1S)-1-(4-bromophenyl)ethyl]cyclopropanecarboxamide (0.134 g, 0.4997 mmol, prepared as described in WO 12001107) in Toluene (6.03 mL) stirred under argon were added Tris(dibenzylideneacetone)dipalladium(0) (9 mg), 4,5-Bis(diphenylphosphino)-9,9-dimethylxanthene (18 mg) and sodium tert-butoxide (96 mg). The mixture was heated in the microwave at 130 C for 15 min. The reaction was then diluted with ethyl acetate and water then brine and then the mixture was extracted with ethyl acetate. The organic layers were combined and dried over magnesium sulphate, filtered then concentrated under reduced pressure to give a yellow oil which was purified by chromatography on column (cyclohexane/EtOAc as solvent) to afford the desired product as a white foam (172 mg).

$^1$H NMR (CDCl3, 400 MHz): d=7.92 (s, 1H), 7.86 (s, 2H), 7.27 (m, 2H), 6.63 (d, J=8.4 Hz, 2H), 5.74 (d, J=7.7 Hz, 1H), 5.09 (t, J=7.3 Hz, 1H), 4.16 (d, J=10.3 Hz, 1H), 3.85 (d, J=10.3 Hz, 1H), 3.60 (d, J=8.1 Hz, 1H), 3.51 (d, J=2.9 Hz, 1H), 2.91-3.03 (m, 1H), 2.61 (d, J=13.6 Hz, 1H), 1.50 (d, J=7.0 Hz, 3H), 1.17-1.34 (m, 1H), 0.90-1.04 (m, 2H), 0.63-0.80 ppm (m, 2H)

EXAMPLE 2

Preparation of N-[(1S)-1-[4-[3-(3,5-dichlorophenyl)-3-(trifluoromethyl)pyrrolidin-1-yl]phenyl]ethyl]cyclopropanecarboxamide

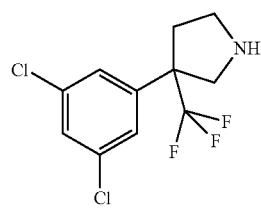

+

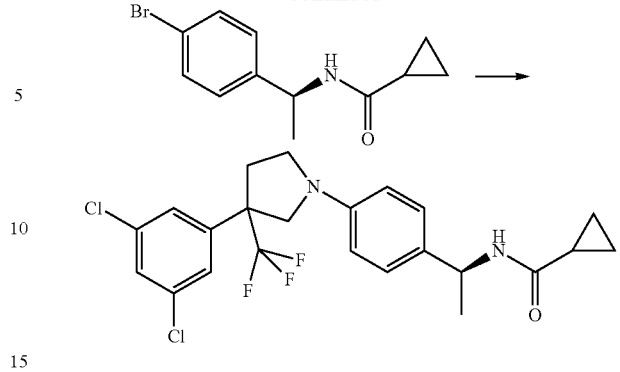

Tris(dibenzylideneacetone)dipalladium(0) (32 mg), 4,5-Bis(diphenylphosphino)-9,9-dimethylxanthene (61 mg) and sodium tert-butoxide (190 mg) were added to a solution of 3-(3,5-dichlorophenyl)-3-(trifluoromethyl)pyrrolidine (520 mg, prepared as described in WO08128711) and N-[(1S)-1-(4-bromophenyl)ethyl]cyclopropanecarboxamide (prepared as described in WO 2012001107, 520 mg) in Toluene (15 mL) under argon atmosphere. The mixture was heated in the microwave at 130 C for 30 min. The reaction was then diluted with ethyl acetate and water then brine and then the mixture was extracted with ethyl acetate. The organic layers were combined and dried over sodium sulphate, filtered then concentrated under reduced pressure to give a yellow oil which was purified by chromatography on column (Heptane/EtOAc as solvent (10/0 to 0/10) to afford the desired product as a white foam (650 mg).

$^1$H NMR (CDCl3, 400 MHz): _=7.40 (s, 1H), 7.31 (s, 2H), 7.26 (m, 2H), 6.62 (d, 2H), 5.73 (d, 1H), 5.09 (t, 1H), 4.06 (d, 1H), 3.85 (d, 1H), 3.57 (m, 1H), 3.50 (m, 1H), 2.84 (m, 1H), 2.56 (m, 1H), 1.50 (d, 3H), 1.2 (m, 1H), 0.99 (m, 2H), 0.72 ppm (m, 2H)

EXAMPLE 3

Preparation of N-[(1S)-1-[4-[5-(3,5-dichlorophenyl)-5-(trifluoromethyl)-4H-isoxazol-3-yl]phenyl]ethyl]acetamide Step 1

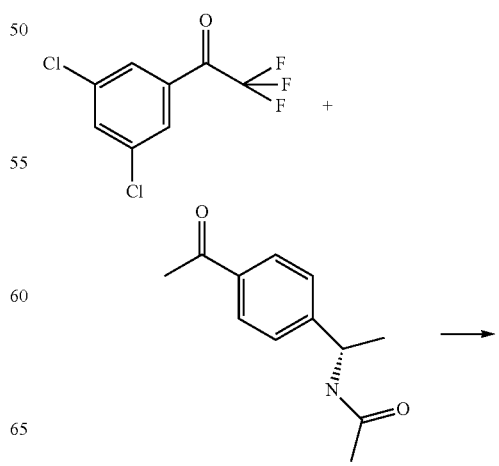

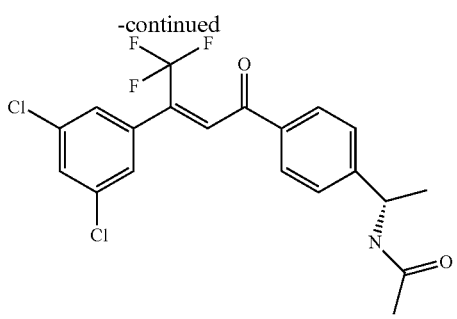

To a suspension of N-[(1S)-1-(4-acetylphenyl)ethyl]acetamide (3 g) and 1-(3,5-dichlorophenyl)-2,2,2-trifluoro-ethanone (3.6 g) in 1,2-dichloroethane (40 mL) was added triethylamine (0.2 mL) and potassium carbonate (1 g). The solution was stirred at 80 C. After 40 minutes, more potassium carbonate (1 g) was added. The solution was heated at 80 C for another 20 minutes then more potassium carbonate (1 g) was added and the suspension was refluxed for 16 hours. The mixture was then cooled to room temperature, then water was added. The mixture was extracted with dichloromethane then washed with brine. The organic layers were combined and dried over magnesium sulphate, filtered then concentrated under reduced pressure to give a yellow oil which was purified by chromatography on column (Heptane/EtOAc as solvent (1/0 to 3/7) to afford the desired product as a yellow oil (5 g).

1H NMR (CDCl3, 400 MHz): ⎕=7.78-7.87 (m, 2H), 7.42-7.40 (m, 2H), 7.33 (m, 1H), 7.16 (d, 2H), 5.69 (d, 1H), 5.02-5.26 (m, 1H), 2.02 (s, 3H), 1.48-1.51 ppm (d, 3H)

Step 2

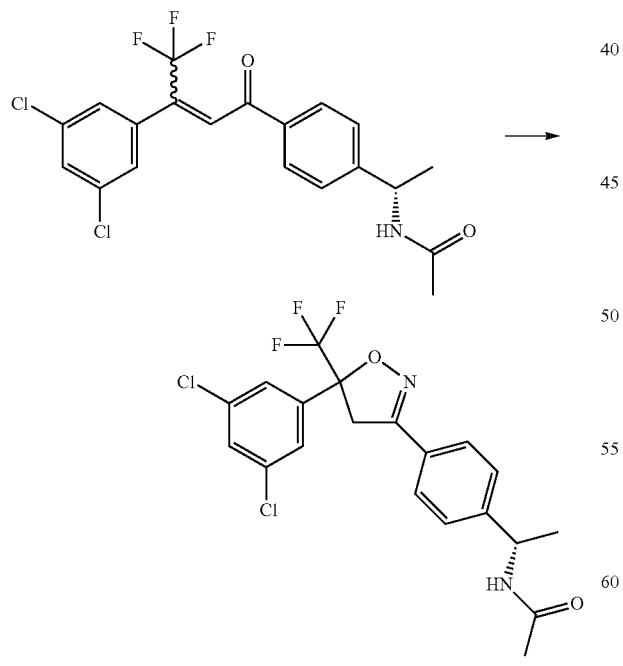

To a solution of N-[(1S)-1-[4-[3-(3,5-dichlorophenyl)-4,4,4-trifluoro-but-2-enoyl]phenyl]ethyl]acetamide (100 mg) in 1,2-dichloroethane (4 mL) was added tetrabutylammonium hydrobromide (40 mg), hydroxylamine (0.03 mL, 50% in water) and sodium hydroxide (0.46 mL, 1M) at room temperature. The solution was stirred at room temperature for 6 hours then a solution of saturated ammonium chloride was added. The mixture was extracted with DCM then washed with brine. The organic layers were combined and dried over magnesium sulphate, filtered then concentrated under reduced pressure to give a yellow oil which was purified by chromatography on column (Heptane/EtOAc as solvent (1/0 to 1/1) to afford the desired product as a yellow oil (77 mg).

$^1$H NMR (CDCl3, 400 MHz): _=7.59-7.69 (m, 2H), 7.49-7.57 (m, 2H), 7.43 (t, J=1.8 Hz, 1H), 7.34-7.41 (m, J=8.4 Hz, 2H), 5.65 (d, J=7.3 Hz, 1H), 5.15 (t, J=7.2 Hz, 1H), 4.01-4.13 (m, 1H), 3.68 (d, J=17.2 Hz, 1H), 2.01 (s, 3H), 1.50 (d, J=7.0 Hz, 3H), 1.27 ppm (t, J=7.2 Hz, 1H).

EXAMPLE 4

Preparation of 2-(1,2,4-triazol-1-yl)-5-[3-(3,4,5-trichlorophenyl)-3-(trifluoromethyl)-2,4-dihydropyrrol-5-yl]benzonitrile Step 1: Preparation of 3-bromo-4-fluoro-N-(trimethylsilylmethyl)benzamide

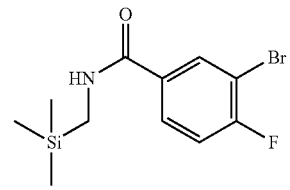 [SMILES: C[Si](C)(C)CNC(=O)c1ccc(F)c(Br)c1]

To a solution of 3-bromo-4-fluoro-benzoic acid (500 mg, 2.2830 mmol) in dichloromethane (15 mL) was added N,N-dimethylpyridin-4-amine (28 mg, 0.22830 mmol), EDCI HCl (570 mg, 2.9679 mmol). To this was added trimethylsilylmethanamine (260 mg, 2.5113 mmol) and reaction was stirred at RT under nitrogen atmosphere for overnight, monitored by TLC. Reaction mass was diluted with water (10 mL), extracted with DCM (3*50 mL). Combined organic layer was dried over sodium sulphate, concentrated under vacuum. Purification by chromatography (hexane/ethyl acetate) provided 3-bromo-4-fluoro-N-(trimethylsilylmethyl)benzamide (550 mg, 80%).

$^1$H NMR (400 MHz, CDCl3): 7.94 (dd, 1H); 7.65 (m, 1H); 7.15 (t, 1H); 5.9 (brs, 1H); 2.94 (d, 2H); 0.12 (s, 9H), LCMS (methanol, ESI): RT=2.06, m/z=302.0 (M–H)

Step 2: Preparation of 3-cyano-4-fluoro-N-(trimethylsilylmethyl)benzamide

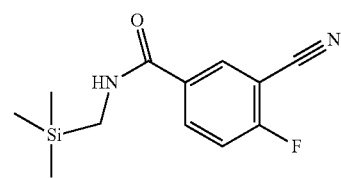 [SMILES: C[Si](C)(C)CNC(=O)c1ccc(F)c(C#N)c1]

In a sealed tube was taken a solution of 3-bromo-4-fluoro-N-(trimethylsilylmethyl)benzamide (10 g, 32.870 mmol) in N,N-dimethylformamide (60 mL) was added zinc formonitrile (7.85 g, 65.740 mmol) followed by palladium(0)tetrakis (triphenylphosphine) (7.61 g, 6.5740 mmol). Reaction was degassed and purged with nitrogen, stirred at 100° C. for 4-5 hrs. Reaction was diluted with water (100 ml) extracted with ethyl acetate (3*100 ml), washed with sodium bicarbonate (50 ml). Combined organic layer was dried over sodium sulphate, concentrated under vacuum. Purification by chromatography (hexane/ethyl acetate) provided 3-cyano-4-fluoro-N-(trimethylsilylmethyl)benzamide (6.7 g, 81%)

$^1$H NMR (400 MHz, CDCl3): 7.98-8.02 (m, 2H); 7.3 (m, 1H); 5.94 (brs, 1H); 2.95-2.98 (m, 2H); 0.13 (s, 9H). LCMS (methanol, APCI): RT=4.11, m/z=249.09 (M−H)

Step 3: Preparation of 3-cyano-4-fluoro-N-(trimethylsilylmethyl)benzenecarbothioamide

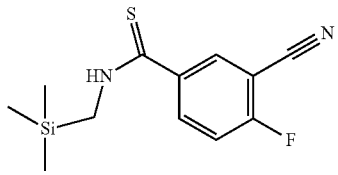 [SMILES: C[Si](C)(C)CNC(=S)c1ccc(F)c(C#N)c1]

A solution of 3-cyano-4-fluoro-N-(trimethylsilylmethyl)benzamide (6.5 g, 26 mmol) and 2,4-bis(4-methoxyphenyl)-2,4-dithioxo-1,3,2,4-dithiadiphosphetane (11 g, 26 mmol) in tetrahydrofuran (75 mL) was refluxed for 2 hrs. Reaction mass was concentrated to remove THF, diluted with water (50 ml), extracted with ethyl acetate (3*100 ml). Combined organic layer was dried over sodium sulphate, concentrated under vacuum. Purification by chromatography (hexane/ethyl acetate) provided 3-cyano-4-fluoro-N-(trimethylsilylmethyl)benzenecarbothioamide (4.8 g, 69%).

$^1$H NMR (400 MHz, CDCl3): 8.2 (m, 1H); 7.93-7.99 (m, 1H); 7.64 (brs, 1H); 7.22 (m, 1H); 3.52 (d, 2H); 0.18 (s, 9H), LCMS (methanol, APCI): RT=4.55, m/z=265.45 (M−H).

Step 4: Preparation of 2-fluoro-5-[3-(3,4,5-trichlorophenyl)-3-(trifluoromethyl)-2,4-dihydropyrrol-5-yl]benzonitrile

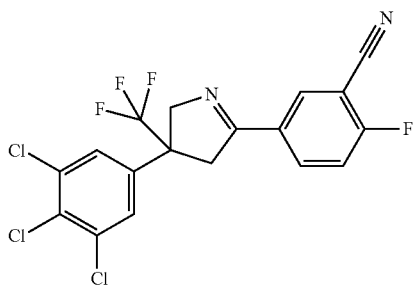 [SMILES: N#Cc1cc(C2=NCC(c3cc(Cl)c(Cl)c(Cl)c3)(C(F)(F)F)C2)ccc1F]

To a solution of 3-cyano-4-fluoro-N-(trimethylsilylmethyl)benzenecarbothioamide (4 g, 15.02 mmol) in N,N-dimethylformamide (40 mL) was added dipotassium carbonic acid (5.26 g, 37.54 mmol). To this was added iodomethane (21.31 g, 150.2 mmol). Reaction mass was stirred at RT for 3 hrs, monitored by TLC. Reaction mass was quenched with water (10 mL), extracted with ethyl acetate (3*50 mL). Combined organic layer was dried over sodium sulphate, concentrated under vacuum to give methyl-3-cyano-4-fluoro-N-(trimethylsilylmethyl)benzenecarboximidothioate. To a −5° C. cooled solution of methyl-3-cyano-4-fluoro-N-(trimethylsilylmethyl)benzenecarboximidothioate (4 g, 14.27 mmol) and 1,2,3-trichloro-5-[1-(trifluoromethyl)vinyl]benzene (3.97 g., 14.41 mmol) in tetrahydrofuran (5 mL) was slowly added tetrabutylammonium hydrofluoride (7.13 ml, 7.133 mmol, 1 mol/L). Reaction was stirred at −5° C. for 30 mins, then allowed to come at RT, and stirred at RT for 2 hrs under Nitrogen atmosphere. Reaction was diluted with water (50 ml), extracted with ethyl acetate (3*100 ml). Combined organic layer was dried over sodium sulphate, concentrated under vacuum. Purification by chromatography (hexane/ethyl acetate) provided 2-fluoro-5-[3-(3,4,5-trichlorophenyl)-3-(trifluoromethyl)-2,4-dihydropyrrol-5-yl]benzonitrile (2.5 g, 40%).

$^1$H NMR (400 MHz, CDCl$_3$): 8.04-8.13 (m, 2H); 7.37 (s, 2H); 7.35 (m, 1H); 4.82 (dd, 1H); 4.36 (d, 1H); 3.7 (dd, 1H); 3.35 (d, 1H), LCMS (methanol, APCI): RT=5.05, m/z=434.88 (M+H)

Step 5: Preparation of 2-(1,2,4-triazol-1-yl)-5-[3-(3,4,5-trichlorophenyl)-3-(trifluoromethyl)-2,4-dihydropyrrol-5-yl]benzonitrile

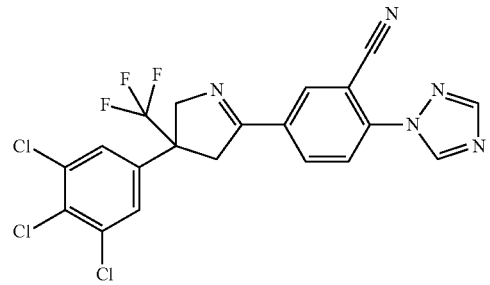 [SMILES: N#Cc1cc(C2=NCC(c3cc(Cl)c(Cl)c(Cl)c3)(C(F)(F)F)C2)ccc1-n1cncn1]

A solution of 2-fluoro-5-[3-(3,4,5-trichlorophenyl)-3-(trifluoromethyl)-2,4-dihydropyrrol-5-yl]benzonitrile (1.0 g, 2.3 mmol), dipotassium carbonic acid (390 mg, 2.8 mmol) and 1H-1,2,4-triazole (190 mg, 2.8 mmol) were heated at 120° C. for 2-3 hrs, monitored by TLC. Reaction was diluted with water (10 ml), extracted with ethyl acetate (3*30 ml). Combined organic layer was dried over sodium sulphate, concentrated under vacuum. Purification by chromatography (hexane/ethyl acetate) provided 2-(1,2,4-triazol-1-yl)-5-[3-(3,4,5-trichlorophenyl)-3-(trifluoromethyl)-2,4-dihydropyrrol-5-yl]benzonitrile as solid (950 mg, 85%). Melting point: 162-164° C.

$^1$H NMR (400 MHz, CDCl$_3$): 8.9 (s, 1H), 8.29-8.34 (m, 2H); 8.21 (s, 1H); 7.93 (d, 1H); 7.40 (s, 2H); 4.94 (d, 1H); 4.51 (d, 1H); 3.84 (d, 1H); 3.54 (d, 1H); LCMS (methanol, APCI): RT=4.96, m/z=483.94 (M+H)

EXAMPLE 5

Preparation of N-[(1S)-1-[4-[5-(3,4,5-trichlorophenyl)-3-(trifluoromethyl)-2,4-dihydropyrrol-3-yl]phenyl]ethyl]cyclopropanecarboxamide

Step 1: Preparation of tert-butyl N-[(1S)-1-(4-bromophenyl)ethyl]carbamate

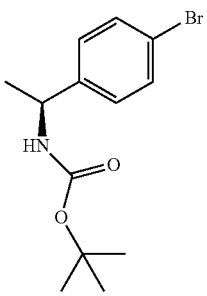 [SMILES: C[C@H](NC(=O)OC(C)(C)C)c1ccc(Br)cc1]

To a stirring solution of compound (1S)-1-(4-bromophenyl)ethanamine (50 mmol) in 50 ml RB and tert-butoxycarbonyl tert-butyl carbonate (50 mmol) was added over period of 20 min and stirring was continued vigorously, After 5 min solid was precipitated out from reaction mass and thus obtained solid was filtered and washed with hexane and dried under vacuum. Weight—13 g (85%)

$^1$H-NMR (400 MHz, CDCl$_3$): 7.45 (2H, d), 7.18 (2H, d), 4.74 (1H, m), 1.40-1.48 (12H, m).

Step 2: Preparation of 4-[(1S)-1-(tert-butoxycarbonylamino)ethyl]benzoic acid

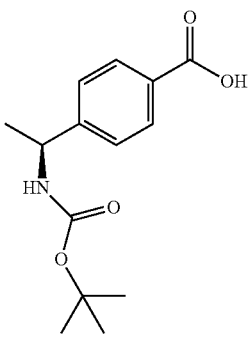 [SMILES: C[C@H](NC(=O)OC(C)(C)C)c1ccc(C(=O)O)cc1]

To a stirring solution of compound tert-butyl N-[(1S)-1-(4-bromophenyl)ethyl]carbamate (1 g, 3.331 mmol) in THF (30 ml) cooled to −78° C., methyl lithium (5.33 mmol, 1.6 eq) was added drop wise under nitrogen atmosphere and stirring was continued for 15 min followed by addition of butyllithium (5.33 mmol, 1.6 eq) drop wise and stirring was continued for 30 min. Dry carbon dioxide was added and stirring continued for 1 h at −70° C. to rt. The reaction mass was quenched with water 50 ml and compound was extracted with ethyl acetate 30 ml×2 in order to remove debromo compound. Aqueous layer was acidified with ammonium chloride and extracted with ehylacetate 30 ml×2 times. The combined organic layers were dried with sodium sulfate and evaporated off under vacuum and dried under vacuum. Weight—0.61 g $^1$H-NMR (400 MHz, CDCl$_3$): 7.86 (2H, d), 7.37 (2H, d), 4.64 (1H, m), 1.28-1.31 (12H, m). LC-MS (methanol, ESI): m/z=264 (M−H), RT 1.95-2.07.

Step 3: Preparation of tert-butyl N-[(1S)-1-[4-(trimethylsilylmethylcarbamoyl)phenyl]ethyl]carbamate

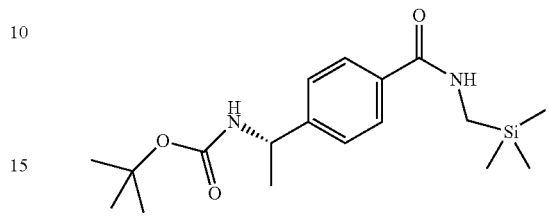

To a stirring solution of 4-[(1S)-1-(tert-butoxycarbonylamino)ethyl]benzoic acid (1 g, 3.769 mmol), 1-hydroxybenzotriazole hydrate (542 mg, 3.5 mmol) in DMF (5 ml), in DCM (30 ml), trimethylsilylmethanamine (0.38 g, 3.7 mmol), trimethylsilylmethanamine (0.38 g, 3.7 mmol) and the reaction mass was cooled to 0° C. and 3-(ethyliminomethyleneamino)-N,N-dimethyl-propan-1-amine hydrochloride (848 mg, 4.4234 mmol) was added and reaction was stirred at 0° C. to RT for overnight. TLC showed reaction was completed. The reaction mass was quenched with water (30 mL) and extracted with DCM (35 ml×2) and combined organic layer was washed with water (20 ml×2) and dried with sodium sulfate and evaporated of under reduced pressure and compound was purified by combiflash. Weight—0.93 g $^1$H-NMR (400 MHz, CDCl$_3$): 7.68 (2H, d), 7.34 (2H, d), 5.93 (1H, m). 4.81 (2H, d), 2.95 (2H, d), 1.40-1.45 (12H, m). LC-MS (methanol, ESI): m/z=349 (M−H), RT 1.95-2.07.

Step 4: Preparation of tert-butyl N-[(1S)-1-[4(trimethylsilylmethylcarbamothioyl)phenyl]ethyl]carbamate

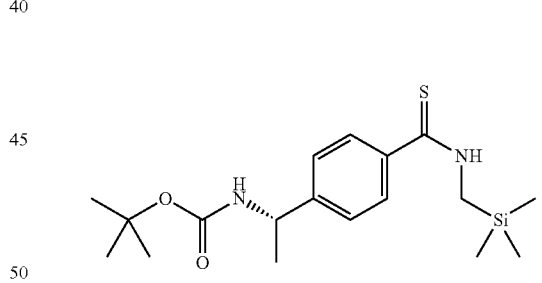

To a solution of tert-butyl N-[(1S)-1-[4-(trimethylsilylmethylcarbamoyl)phenyl]ethyl]carbamate (1 g, 2.853 mmol) in THF (25 ml) was added 2,4-bis(4-methoxyphenyl)-1,3,2,4-dithiadiphosphetane-2,4-disulfide (1 eq, 2.853 mmol) and reaction mass was stirred at 65° C. for 4 h. TLC showed reaction was completed. The solvent was removed from the reaction mass on rotary evaporator and resultant reaction mass was diluted with ethyl acetate, washed with water (twice). The organic layer was dried over anhydrous sodium sulfate and concentrated under reduced pressure. Crude mass thus obtained was purified by combiflash (silica gel). Weight—0.8 g $^1$H-NMR (400 MHz, CDCl$_3$): 7.65 (2H, d), 7.51-7.52 (1H, m), 7.30 (2H, d), 4.76-4.81 (2H, m), 3.51 (2H, d), 1.40-1.45 (12H, m). LC-MS (methanol, ESI): m/z=365 (M−H), RT 2.51-2.57.

Step 5: Preparation of tert-butyl N-[(1S)-1-[4-[5-(3,4,5-trichlorophenyl)-3-(trifluoromethyl)-2,4-dihydropyrrol-3-yl]phenyl]ethyl]carbamate

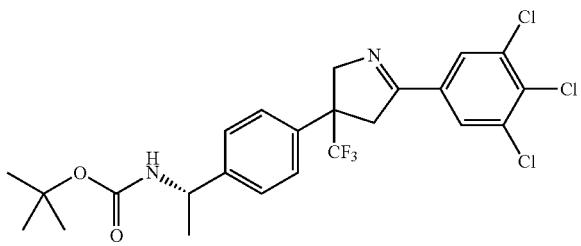 [SMILES: C[C@H](NC(=O)OC(C)(C)C)c1ccc(C2(C(F)(F)F)CN=C(c3cc(Cl)c(Cl)c(Cl)c3)C2)cc1]

To stirring solution of compound tert-butyl N-[(1S)-1-[4-(trimethylsilylcarbamothioyl)phenyl]ethyl]carbamate (0.5 g, 1 mmol) in DMF (25 ml), potassium carbonate (2 eq., 2 mmol) was added followed by addition of iodomethane (10 equiv., 10 mmol) over period of 1 hr and stirring was continued for 3 h. After completion of reaction (monitored by TLC) reaction mass was diluted with ethyl acetate and washed with water (20 ml×3 times) and dried with sodium sulphate and evaporated off under vacuum. Thus obtained reaction mass was taken into THF (25 ml) and 1,2,3-trichloro-5-[1-(trifluoromethyl)vinyl]benzene (1 equiv., 1 mmol) was added into it. The mixture was cooled to 0° C., TBAF (1 eq, 1 mmol) was added and stirring was continued for 3 h at to rt.

After completion of reaction (monitored by TLC), solvent was evaporated off under vacuum and reaction mass was diluted with ethyl acetate and washed with water (30 ml×2 times) and dried with sodium sulphate and evaporated off under vacuum. Compound was purified by combiflash, (25-30% EtOAC-hexane). Weight—0.11 g (20%)

¹H-NMR (400 MHz, CDCl₃): 7.97 (2H, d), 7.33-7.56 (4H, m), 4.85-4.92 (2H, m), 4.50 (1H, dd), 3.91 (1H, dd), 3.58 (1H, dd), 1.40-1.45 (12H, m). LC-MS (methanol, ESI): m/z=533 (M−H), RT 2.51-2.57.

Step 6: Preparation of N-[(1S)-1-[4-[5-(3,4,5-trichlorophenyl)-3-(trifluoromethyl)-2,4-dihydropyrrol-3-yl]phenyl]ethyl]cyclopropanecarboxamide

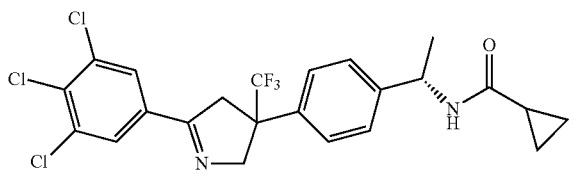 [SMILES: C[C@H](NC(=O)C1CC1)c1ccc(C2(C(F)(F)F)CN=C(c3cc(Cl)c(Cl)c(Cl)c3)C2)cc1]

To a solution of tert-butyl N-[(1S)-1-[4-[5-(3,4,5-trichlorophenyl)-3-(trifluoromethyl)-2,4-dihydropyrrol-3-yl]phenyl]ethyl]carbamate (0.35 g) in DCM (20 ml) was added 2,2,2-trifluoroacetic acid (3 equiv) and reaction mass was stirred for 5 h at RT. After completion of the reaction, solvent was removed under vaccuo and compound thus obtained was directly taken for the next step. A Solution of (1S)-1-[4-[5-(3,4,5-trichlorophenyl)-3-(trifluoromethyl)-2,4-dihydropyrrol-3-yl]phenyl]ethanamine TFA salt (0.3 g, 0.7 mmol), in DCM (20 ml) was cooled at 0° C. To the cooled mixture was added triethylamine (2.2 eq, 1.54 mmol) followed by dropwise addition of cyclopropane carboxylic acid chloride (1 equiv, 0.7 mmol) over period of 5 min and stirring was continued for overnight. After completion of reaction (monitored by TLC), reaction mass was diluted with DCM (20 ml) and washed with water (20 ml). The organic layer was then dried over anhydrous sodium sulphate, and the solvent was removed under vacuum. Compound was purified by Combiflash (35% EtOAC-hexane) Weight—0.2 g, MPt. 80-82° C.

¹H-NMR (400 MHz, CDCl₃): 7.82 (2H, d), 7.35-7.41 (4H, m), 6.05 (1H, m), 5.13 (1H, m), 4.86 (1H, dd), 4.42 (1H, dd), 3.78 (1H, dd), 3.45 (1H, dd). 1.46-1.50 (4H, m), 0.93-0.96 (2H, m), 0.72-0.731 (2H, m) LC-MS (methanol, ESI): m/z=501 (M−H), RT 2.23-2.30.

EXAMPLE 6

Preparation of N-{2-bromo-4-[4-(3,5-dichlorophenyl)-4-trifluoromethyl-4,5-dihydro-3H-pyrrol-2yl]-benzyl}acetamide

Step 1: Bromination of 3-bromo-4-methyl benzoic acid

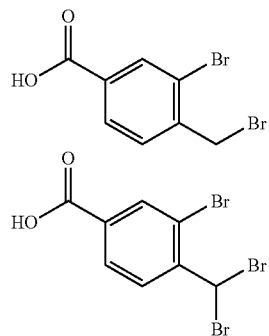

3-bromo-4-methyl benzoic acid (10 g, 46.72 mmol), NBS (8.7 g, 49.15 mmol)) and benzoylperoxide (0.5 g, 2 mmol)) were suspended in CCl4 and then heated to reflux for 5 hrs. After completion of the reaction (TLC monitoring) water was added into the reaction mixture. The organic layer was separated, dried over anhydrous sodium sulphate and concentrated in vaccuo. The crude mixture thus obtained containing 3-bromo-4-bromomethyl benzoic acid and the 3-bromo-4-dibromomethyl benzoic acid was taken directly into the next step.

LC-MS (methanol, ESI): m/z=291 (M−H) and 368 (M−H)

Step 2: Preparation of 3-bromo-4-(dibromomethyl)-N-[(trimethylsilyl)methyl]benzamide

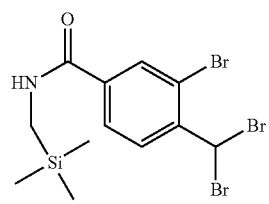 [SMILES: C[Si](C)(C)CNC(=O)c1ccc(C(Br)Br)c(Br)c1]

A mixture of 3-bromo-4-(bromomethyl)-N-[(trimethylsilyl)methyl]benzamide and 3-bromo-4-(dibromomethyl)-N-[(trimethylsilyl)methyl]benzamide (19 g, 51 mmol), 1-(trimethylsilyl)methylamine (5.78 g, 56 mmol), N,N-dimethylaminopyridine (0.1 g) and N-(3-dimethylaminopropyl)-N'-ethylcarbodiimide.HCl (12.74 g, 66 mmol) was dissolved in tetrahydrofuran solvent and stirred for 1 h at rt. After completion of the reaction (TLC monitoring), Reaction mixture was concentrated on rotary evaporator. Water was added to the reaction mixture, and extracted with ethylacetate. The organic layer was separated and dried using sodium sulphate. The residue was purified by silica gel chromatography to obtain 3-bromo-4-(dibromomethyl)-N-[(trimethylsilyl) methyl]benzamide (16 g).

3-bromo-4-(dibromomethyl)-N-[(trimethylsilyl)methyl] benzamide.

LC-MS (methanol, ESI): m/z=456 (M+H).

1H-NMR (400 MHz, CDCl3): 8.01 (1H, dd), 7.87 (1H, d), 7.04 (1H, dd), 6.13 (1H, bs), 3.51 (2H, d), 0.17 (9H, s).

Step 3: Preparation of 3-bromo-4-formyl-N-[(trimethylsilyl)methyl]benzamide

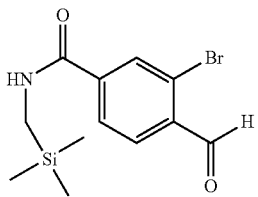

Compound B (3-bromo-4-(dibromomethyl)-N-[(trimethylsilyl)methyl]benzamide) (0.25 g, 0.69 mmol) was taken in acetone (5 ml) and water (2.5 ml). Silver nitrate (0.3 g, 1.7 mmol) was added to the reaction mixture. The reaction was stirred at rt for 6 hrs. The reaction mass was then concentrated and extracted with ethylacetate. The organic layer was separated and dried using sodium sulphate. The organic layer was concentrated to obtain the product 3-bromo-4-formyl-N-[(trimethylsilyl)methyl]benzamide. (0.15 g). LC-MS (methanol, ESI): m/z=314 (M+H).

1H-NMR (400 MHz, CDCl3): 10.33 (1H, s), 7.90 (1H, m), 7.60 (1H, dd), 7.56 (1H, m), 5.99 (1H, s), 2.99 (2H, d), 0.17 (9H, s).

Step 4: Preparation of 3-bromo-4-hydroxymethyl-N-[trimethylsilaylmethyl]benzamide

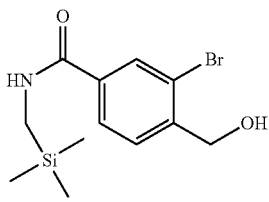 [SMILES: C[Si](C)(C)CNC(=O)c1ccc(CO)c(Br)c1]

3-bromo-4-formyl-N-[(trimethylsilyl)methyl]benzamide (0.1 g, 0.3 mmol) was dissolved in methanol and to this was added NaBH4 (0.014 g, 0.38 mmol). Reaction was stirred at rt for 1 hr. Methanol was removed under vaccuo and water was added to the reaction mass which was then extracted using ethyl acetate. The organic layer was seperated and dried using sodium sulphate followed by concentration to get the product 3-bromo-4-hydroxymethyl-N-[trimethylsilaylmethyl]benzamide (0.05 g).

LC-MS (methanol, ESI): m/z=316 (M+H).

1H-NMR (400 MHz, CDCl3): 7.90 (1H, m), 7.60 (1H, m), 7.53 (1H, m), 6.02 (1H, s), 4.75 (2H, s), 2.99 (2H, s), 0.17 (9H, s).

Step 5: Preparation of Acetic acid 2-bromo-4-(trimethylsilanylmethyl-carbamoyl)-benzylester

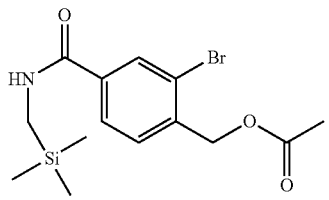 [SMILES: CC(=O)OCc1ccc(C(=O)NC[Si](C)(C)C)cc1Br]

3-bromo-4-hydroxymethyl-N-[trimethylsilaylmethyl] benzamide (0.25 g, 0.7 mmol) was dissolved in DMF solvent, triethyl amine (0.159 g, 1.5 mmol) and acetyl chloride (0.061 g, 0.8 mmol) were added to the reaction mixture at rt. The reaction was stirred at rt for 30 min. Water was added and reaction mass was then extracted with ethyl acetate. The organic layer was separated, dried using sodium sulphate and concentrated to get the product Acetic acid 2-bromo-4-(trimethylsilanylmethyl-carbamoyl)-benzylester (0.15 g).

LC-MS (methanol): m/z=358 (M+H).

1H-NMR (400 MHz, CDCl3): 7.90 (1H, m), 7.60 (1H, m), 7.38 (1H, m), 6.14 (1H, bs), 5.11 (2H, s), 2.99 (2H, d), 2.15 (3H, s), 0.17 (9H, s).

Step 6: Preparation of 3-bromo-4-(2-oxo-propyl)-N-trimethylsilanylmethyl-thiobenzamide

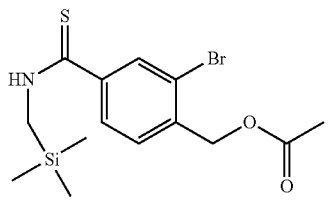 [SMILES: CC(=O)OCc1ccc(C(=S)NC[Si](C)(C)C)cc1Br]

Acetic acid 2-bromo-4-(trimethylsilanylmethyl-carbamoyl)-benzylester (2.4 g, 7.6 mmol) and Lawesson reagent (2.7 g, 6.6 mmol) were suspended in THF. The mixture was heated to reflux for 3 hrs, concentrated, washed with water and extracted with ethyl acetate. The organic layer was separated and dried using sodium sulphate. The residue was purified by silica gel chromatography to obtain 3-bromo-4-(2-oxo-propyl)-N-trimethylsilanylmethyl-thiobenzamide (1.8 g).

LC-MS (methanol, ESI): m/z=374 (M+H).

1H-NMR (400 MHz, CDCl3): 7.90 (1H, m), 7.60 (1H, m), 7.38 (1H, m), 6.01 (1H, br s), 5.11 (2H, d), 2.99 (2H, d), 2.15 (3H, s), 0.17 (9H, s)

Step 7: Preparation of Acetic acid 2-bromo-4-[4-(3,5-dichlorophenyl)-4-trifluoromethyl-4,5-dihydro-3H-pyrrol-2yl]-benzylester

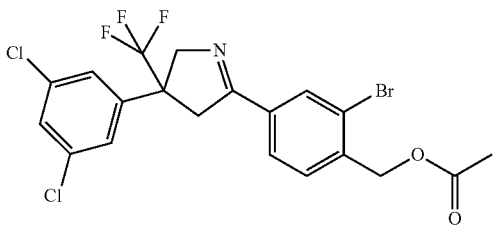 [SMILES: CC(=O)OCc1ccc(C2=NCC(c3cc(Cl)cc(Cl)c3)(C(F)(F)F)C2)cc1Br]

A mixed solution of methyliodide (0.69 g, 4.8 mmol), potassium carbonate (0.80 g, 5.7 mmol) and 3-bromo-4-(2-oxo-propyl)-N-trimethylsilanylmethyl-thiobenzamide (1.8 g, 5.4 mmol) in DMF (25 ml) was stirred at 0° C. for 4 hrs. The reaction mixture was poured into ice-cold water, extracted with ethyl acetate. The organic layer was separated, dried using sodium sulphate and concentrated to get the crude Acetic acid 2-bromo-4{methylsulfanyl-[(E)-trimethylsilanylmethylimino]-methyl}-benzyl ester. (0.95 g) which was dissolved in THF and was cooled to 0° C. under N2 atm. A solution of TBAF (1.0M in THF) (0.56 ml) was added gradually into it and reaction mixture was stirred for 8 hrs at rt. The reaction mass was then concentrated and extracted with ethylacetate. The organic layer was separated and dried using sodium sulphate. The resulting mixture was then purified by silica gel chromatography to obtain Acetic acid 2-bromo-4-[4-(3,5-dichlorophenyl)-4-trifluoromethyl-4,5-dihydro-3H-pyrrol-2yl]-benzylester (1.1 g). LC-MS (methanol, ESI): m/z=508 (M+H).

$^1$H-NMR (400 MHz, CDCl3): 8.07 (1H, m), 7.71 (1H, m), 7.47 (1H, m), 7.38 (1H, m), 7.24 (2H, m), 5.23 (2H, s), 4.90 (1H, m), 4.43 (1H, d), 3.75 (1H, m), 3.43 (1H, d), 2.17 (3H, s).

Step 8: Preparation of 2-bromo-4-[4-(3,5-dichlorophenyl)-4-trifluoromethyl-4,5-dihydro-3H-pyrrol-2yl]-phenyl-methanol

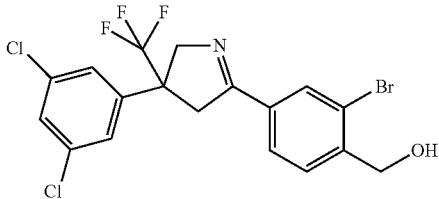 [SMILES: OCc1ccc(C2=NCC(c3cc(Cl)cc(Cl)c3)(C(F)(F)F)C2)cc1Br]

To a solution of Acetic acid 2-bromo-4-[4-(3,5-dichlorophenyl)-4-trifluoromethyl-4,5-dihydro-3H-pyrrol-2yl]-benzylester (1.1 g, 2.1 mmol) in methanol (20 ml) was added sodium methoxide (0.1 g, 1.85 mmol) and the solution was stirred for 1 h at rt. The reaction mass was then concentrated and extracted with ethylacetate. The organic layer was separated and dried using sodium sulphate. The resulting mixture was then purified by silica gel chromatography to obtain 2-bromo-4-[4-(3,5-dichlorophenyl)-4-trifluoromethyl-4,5-dihydro-3H-pyrrol-2yl]-phenyl-methanol (0.95 g). LC-MS (methanol, ESI): m/z=466 (M+H).

$^1$H-NMR (400 MHz, CDCl3): 8.07 (1H, m), 7.78 (1H, m), 7.59 (1H, m), 7.38 (3H, m), 4.90 (3H, d), 4.43 (1H, d), 3.75 (1H, m), 3.43 (1H, d).

Step 9: Preparation of Methanesulfonic acid-2-bromo-4-[4-(3,5-dichlorophenyl)-4-trifluoromethyl-4,5-dihydro-3H-pyrrol-2yl]-benzylester

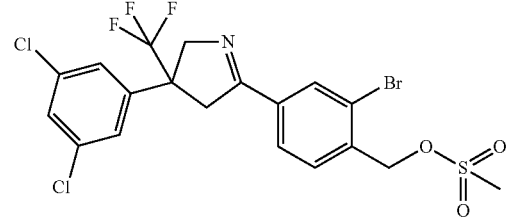 [SMILES: CS(=O)(=O)OCc1ccc(C2=NCC(c3cc(Cl)cc(Cl)c3)(C(F)(F)F)C2)cc1Br]

To a solution of 2-bromo-4-[4-(3,5-dichlorophenyl)-4-trifluoromethyl-4,5-dihydro-3H-pyrrol-2yl]-phenyl-methanol (0.95 g, 2 mmol) and triethylamine (0.4 g, 4.0 mmol) in THF was added methanesulfonyl chloride (0.35 g, 3.0 mmol) gradually. The mixture was stirred for 1 hr at rt. The reaction mixture was washed with water. The organic layer was separated and dried using sodium sulphate. The organic layer was evaporated to get the solid compound Methanesulfonic acid-2-bromo-4-[4-(3,5-dichlorophenyl)-4-trifluoromethyl-4,5-dihydro-3H-pyrrol-2yl]-benzylester (0.9 g).

LC-MS (methanol, ESI): m/z=544 (M+H).

$^1$H-NMR (400 MHz, CDCl3): 8.13 (1H, m), 7.81 (1H, m), 7.58 (1H, m), 7.38 (1H, m), 7.24 (2H, m), 5.36 (2H, s), 4.90 (1H, m), 4.43 (1H, d), 3.75 (1H, m), 3.43 (1H, d), 3.04 (3H, s).

Step 10: Preparation of 2-bromo-4-[4-(3,5-dichlorophenyl)-4-trifluoromethyl-4,5-dihydro-3H-pyrrol-2yl]-benzylamine

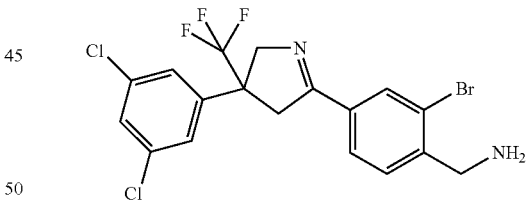

To a solution of Methanesulfonic acid-2-bromo-4-[4-(3,5-dichlorophenyl)-4-trifluoromethyl-4,5-dihydro-3H-pyrrol-2yl]-benzylester (1.0 g, 1.8 mmol) in THF (30 mL) and MeOH (30 mL) was added dropwise to a mixed solution of aq. ammonia (30%), 30 ml), and the reaction was stirred for 12 hrs at rt. The reaction mass was then concentrated and extracted with ethylacetate. The organic layer was separated and dried using sodium sulphate. The organic layer was evaporated to get the gummy compound 2-bromo-4-[4-(3,5-dichlorophenyl)-4-trifluoromethyl-4,5-dihydro-3H-pyrrol-2yl]-benzylamine.

LC-MS (methanol, ESI): m/z=467 (M+H).

$^1$H-NMR (400 MHz, CDCl3): 8.07 (1H, m), 7.71 (1H, m), 7.59 (1H, m), 7.38 (1H, m), 7.24 (2H, m), 4.90 (1H, d), 4.43 (3H, m), 3.75 (1H, m), 3.43 (1H, d).

Step 11: Preparation of N-{2-bromo-4-[4-(3,5-dichlorophenyl)-4-trifluoromethyl-4,5-dihydro-3H-pyrrol-2yl]-benzyl}acetamide

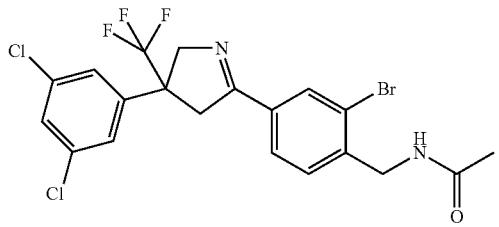 [SMILES: CC(=O)NCc1ccc(C2=NCC(c3cc(Cl)cc(Cl)c3)(C(F)(F)F)C2)cc1Br]

To a solution of 2-bromo-4-[4-(3,5-dichlorophenyl)-4-trifluoromethyl-4,5-dihydro-3H-pyrrol-2yl]-benzylamine (0.15 g, 0.32 mmol) in THF was added acetic anhydride (0.04 g, 0.39 mmol) and the mixture was stirred at rt for 1 hr. The reaction mass was then concentrated under reduced pressure and extracted with ethylacetate. The organic layer was separated and dried using sodium sulphate. The resulting mixture was then purified by silica gel chromatography to obtain N-{2-bromo-4-[4-(3,5-dichlorophenyl)-4-trifluoromethyl-4,5-dihydro-3H-pyrrol-2yl]-benzyl}acetamide.

LC-MS (methanol, ESI): m/z=509 (M+H).

$^1$H-NMR (400 MHz, CDCl3): 8.07 (1H, m), 7.71 (1H, m), 7.47 (1H, m), 7.38 (1H, m), 7.24 (2H, m), 5.98 (1H, s), 4.90 (1H, d), 4.43 (3H, m), 3.75 (1H, m), 3.43 (1H, d), 2.04 (3H, s).

EXAMPLE 7

Preparation of N-{4-[3-(3,5-dichlorophenyl)-3-(trifluoromethyl)pyrrolidin1-yl]-2-methyl-benzyl)acetamide Step 1: Preparation of 1-Benzyl-3-(3,5-dichlorophenyl)-3-(trifluoromethyl)pyrrolidine

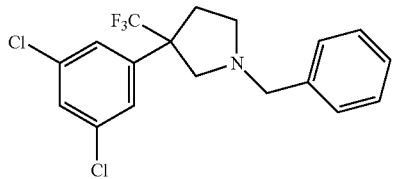 [SMILES: FC(F)(F)C1(c2cc(Cl)cc(Cl)c2)CCN(Cc2ccccc2)C1]

To a cooled solution of 1,3-dichloro-5(1-trifluoromethyl)vinyl)benzene (0.5 g, 2.0 mmol) and N-benzyl-1-methoxy-N-9trimethylsilyl)methyl)methanamine (0.4 g, 2.0 mmol) in DCM (10 mL) was added dropwise a solution of TFA (0.024 g, 0.2 mmol) in DCM (1 mL). The reaction mixture was stirred for 3 hrs at rt. The organic layer was washed with water (2×10 mL) and 10% aq sodium carbonate solution (10 mL). The organic layer was separated, dried with sodium sulphate and concentrated under reduced pressure The residue was purified by silica gel chromatography to yield 1-Benzyl-3-(3,5-dichlorophenyl)-3-(trifluoromethyl)pyrrolidine (0.5 g).

LC-MS (methanol, ESI): m/z=374 (M+H).

$^1$H-NMR (400 MHz, CDCl3): 7.36 (4H, m), 7.30 (2H, m), 7.23 (2H, m), 3.67 (2H, s), 3.08 (2H, dd), 2.69 (2H, m), 2.53 (1H, m), 2.27 (1H, m).

Step 2: Preparation of 3-(3,5-dichlorophenyl)-3-(trifluoromethyl)pyrrolidine

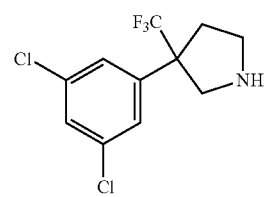 [SMILES: FC(F)(F)C1(c2cc(Cl)cc(Cl)c2)CCNC1]

To a solution of 1-Benzyl-3-(-(3,5-dichlorophenyl)-3-(trifluoromethyl)pyrrolidine (0.22 g, 0.59 mmol) and 1-chloroethylchloroformate (0.17 g, 1.2 mmol) in DCM was heated for reflux for 3 hrs. The mixture was cooled to rt and concentrated under reduced pressure. Methanol was added to the residue which was then heated with stirring for 3 hrs at 60° C. The mixture was concentrated and water was added to it. The residue was extracted with ethylacetate (20 ml×3) washed with brine, dried over sodium sulphate and concentrated under reduced pressure. Purification over silica gel yielded 3-(3,5-dichlorophenyl)-3-(trifluoromethyl)pyrrolidine (4.2 g).

LC-MS (methanol, ESI): m/z=284 (M+H).

$^1$H-NMR (400 MHz, CDCl3): 7.35 (1H, t), 7.25 (2H, d), 3.74 (1H, d), 3.19 (2H, m), 2.97 (1H, m), 2.53 (1H, m), 2.27 (1H, m).

Step 3: Preparation of N-(4-bromo-2-methyl-benzyl)acetamide

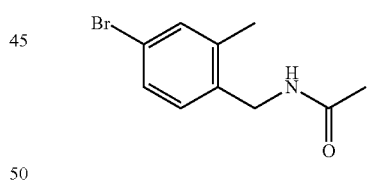

4-bromo-2-methyl benzonitrile (2.0 g, 0.01 mol) was taken in methanol along with NiCl2 (2.41 g, 0.01 mol). In the same pot acetic anhydride was taken (2.0 g, 0.020 mol). The reaction was cooled to 0° C. NaBH4 (2.7 g, 0.07 mol) was added slowly to the reaction while stirring at the same temperature for 1 hr. The reaction mixture was concentrated under reduced pressure and was extracted with ethylacetate. The organic layer was separated, dried using sodium sulphate and concentrated under reduced pressure. The residue thus obtained was purified by silica gel chromatography to yield N-(4-bromo-2-methyl-benzyl)acetamide. (1.1 g).

LC-MS (methanol, ESI): m/z=242 (M+H).

1H-NMR (400 MHz, CDCl3): 7.71 (1H, m), 7.47 (1H, m), 7.38 (1H, m), 5.98 (1H, s), 3.75 (1H, m), 3.43 (1H, d), 2.31 (3H, s), 2.04 (3H, s).

Step 4: Preparation of N-{4-[3-(3,5-dichlorophenyl)-3-(trifluoromethyl)pyrrolidin1-yl]-2-methylbenzyl)acetamide

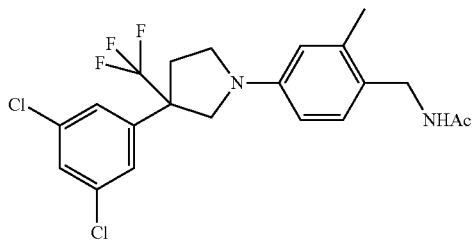 [SMILES: CC(=O)NCc1ccc(N2CCC(c3cc(Cl)cc(Cl)c3)(C(F)(F)F)C2)cc1C]

To the mixture of 3-(3,5-dichlorophenyl)-3-(trifluoromethyl)pyrrolidine (0.25 g, 0.88 mmol) and the N-(4-bromo-2-methyl-benzyl)acetamide (0.8 g, 0.7 mmol) in anhydrous toluene under N2 atm was added Tris (dibenzylidineacetone) dipalladium (0.02 g, 0.02 mmol) and the ligand xanthphos (0.03 g, 0.053 mmol) followed by the addition of sodium tertiary butoxide (0.127 g, 1.3 mmol). The reaction mixture was heated at 80° C. for 3 hrs. After completion of the reaction (TLC monitoring), reaction mass filtered over celite. The filtrate was concentrated and purified using column chromatography.

LC-MS (methanol, ESI): m/z=445 (M+H).

1H-NMR (400 MHz, CDCl3): 7.37 (1H, d), 7.29 (2H, m), 7.11 (1H, d), 6.41 (2H, m), 5.45 (1H, b s), 4.35 (2H, s), 4.01 (1H, d), 3.75 (1H, d), 3.43 (2H, m), 2.81 (1H, d), 2.51 (1H, d), 2.31 (3H, s), 1.97 (3H, s).

The following examples have been prepared according to methods described in US2009/0156643 and analysed by the LCMS methods described below:

Method A:
ZQ Mass Spectrometer from Waters (Single quadrupole mass spectrometer)
Instrument Parameter:
Ionization method: Electrospray
Polarity: positive and negative ions
Capillary: 3.00 kV
Cone: 30.00 V
Extractor: 2.00 V
Source Temperature: 100° C.,
Desolvation Temperature: 250° C.
Cone Gas Flow: 50 L/Hr
Desolvation Gas Flow: 400 L/Hr
Mass range: 100 to 900 Da
HP 1100 HPLC from Agilent:
Solvent degasser, quaternary pump, heated column compartment and diode-array detector.
Column: Phenomenex Gemini C18, 3 _m, 30×3 mm,
Temp: 60° C.
DAD Wavelength range (nm): 210 to 500
Solvent Gradient:

A=H2O+5% MeOH+0.05% HCOOH

B=Acetonitril+0.05% HCOOH

| Time | A % | B % | Flow (ml/min) |
|---|---|---|---|
| 0.00 | 100 | 0 | 1.700 |
| 2.00 | 0 | 100.0 | 1.700 |
| 2.80 | 0 | 100.0 | 1.700 |

-continued

| Time | A % | B % | Flow (ml/min) |
|---|---|---|---|
| 2.90 | 100 | 0 | 1.700 |
| 3.00 | 100 | 0 | 1.700 |

Method B:
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the following HPLC gradient conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC BEH C18; Column length: 50 mm; Internal diameter of column: 2.1 mm; Particle Size: 1.7 micron; Temperature: 60° C.

EXAMPLE 8

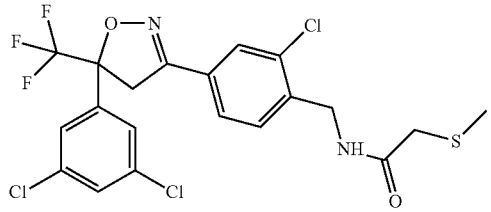 [SMILES: CSCC(=O)NCc1ccc(C2=NOC(c3cc(Cl)cc(Cl)c3)(C(F)(F)F)C2)cc1Cl]

Method A RT 2.17 min, MH+ 511

EXAMPLE 9

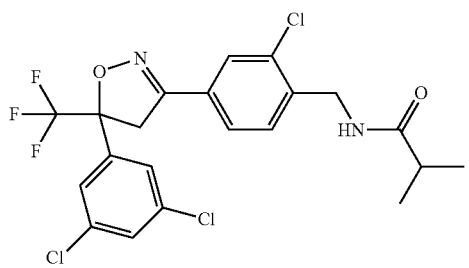 [SMILES: CC(C)C(=O)NCc1ccc(C2=NOC(c3cc(Cl)cc(Cl)c3)(C(F)(F)F)C2)cc1Cl]

Method A RT 2.19 min, MH+ 493

EXAMPLE 10

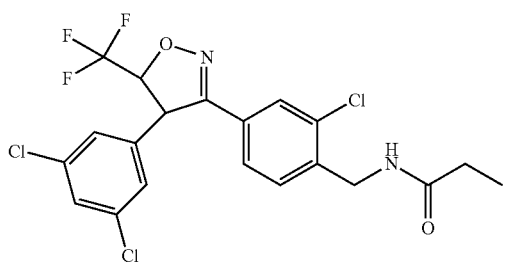 [SMILES: CCC(=O)NCc1ccc(C2=NOC(C(F)(F)F)C2c2cc(Cl)cc(Cl)c2)cc1Cl]

Method B RT 1.98 min, MH+ 479

The following Examples have been prepared according to methods described in WO2008/150393

EXAMPLE 11

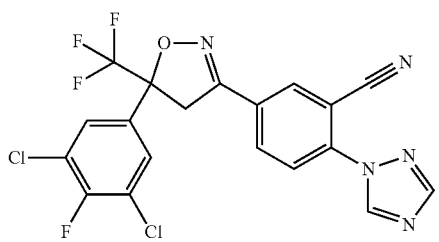 [SMILES: N#Cc1cc(C2=NOC(c3cc(Cl)c(F)c(Cl)c3)(C(F)(F)F)C2)ccc1-n1cncn1]

Method A RT 2.1 min, MH+ 470

The following example have been prepared according to methods described in WO2009/051956

EXAMPLE 12

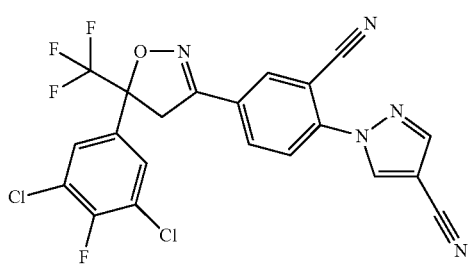 [SMILES: N#Cc1cnn(-c2ccc(C3=NOC(c4cc(Cl)c(F)c(Cl)c4)(C(F)(F)F)C3)cc2C#N)c1]

1H NMR in CDCl3: 3.73 ppm (d, 1H), 4.12 ppm (d, 1H), 7.58 ppm (d, 2H), 7.93 (m, 1H), 8.07-8.12 (m, 3H), 8.62 (s, 1H)

TABLE A

Compounds of formula Ia (Ia)

| | B1—B2—B3 | R2 | R5 | R8 |
|---|---|---|---|---|
| A1 | C=N—O | 3,5-dichlorophenyl | chloro | —CH$_2$—S—CH$_3$ |
| A2 | C=N—O | 3,5-dichlorophenyl | chloro | —CH(CH$_3$)CH$_3$ |
| A3 | C=N—O | 3,5-dichlorophenyl | chloro | —CH$_2$CH$_3$ |
| A4 | N—CH$_2$—CH$_2$ | 3,5-dichlorophenyl | methyl | —CH$_3$ |
| A5 | C=N—CH$_2$ | 3,5-dichlorophenyl | bromo | —CH$_3$ |
| A6 | C=N—CH$_2$ | 3,5-dichlorophenyl | bromo | —CH$_2$CH$_3$ |
| A7 | C=N—CH$_2$ | 3,5-dichlorophenyl | bromo | cyclopropyl |

TABLE B

Compounds of formula Ib*

(Ib*)

| | B1—B2—B3 | R2 | R8 |
|---|---|---|---|
| B1 | N—CH$_2$—CH$_2$ | 3,5-dichlorophenyl | cyclopropyl |
| B2 | C=N—O | 3,5-dichlorophenyl | —CH$_3$ |
| B3 | C=N—CH$_2$ | 3,4,5-trichlorophenyl | cyclopropyl |
| B4 | N—CH$_2$—CH$_2$ | 3,5-di-trifluoromethylphenyl | cyclopropyl |

TABLE C

Compounds of formula Ic (Ic)

| | B1—B2—B3 | R2 |
|---|---|---|
| C1 | N—CH$_2$—CH$_2$ | 3,5-dichlorophenyl |
| C2 | C=N—CH$_2$ | 3,4,5-trichlorophenyl |
| C3 | C=N—O | 3,5-dichloro-4-fluorophenyl |

TABLE D

Compounds of formula Id (Id)

| B1—B2—B3 | R2 | Z |
|---|---|---|
| D1 | C=N—O | 3,5-dichloro-4-fluorophenyl | cyano |

BIOLOGICAL EXAMPLES

*Euschistus heros* (Neotropical brown stink bug) (contact/feeding activity)

2 week old soybean plants are sprayed in a turn table spray chamber with the diluted spray solutions. After drying, 2 soybean seeds are added and plants are infested with 10 N-2 nymphs of the neotropical brown stink bug *Euschistus heros* in plastic test boxes. Boxes are incubated in a climate chamber at 25° C. and 60% RH. Evaluation is done 5 days after infestation on mortality and growth effects.

The following gave at least 50% control at 50 ppm: A1, A2, A3, A4, A5, B1, B2, B3, B4, C2, C3, D1

The following compounds gave more than 80% control at 50 ppm: A1, A3, B1, B2, B3, B4, C2, C3, D1.

Compounds C2, C3 and D1 demonstrated excellent control at low application rates.

The invention claimed is:

1. A method of controlling and/or preventing infestation of *Euschistus heros* in soybean, the method comprising applying to a crop of soybean plants, the locus thereof, or propagation material thereof, a compound of formula IC

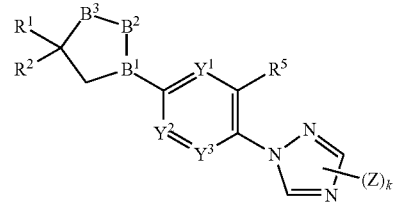

(IC)

wherein
$R^5$ is cyano;
Z is cyano or trifluoromethyl;
$R^1$ is $CF_3$;
—$B^1$—$B^2$—$B^3$— is —C=N—O— or —C=N—$CH_2$—;
$Y^1$, $Y^2$ and $Y^3$ are CH;
k is 0;
$R^2$ is 3,5-dichlorophenyl-, 3,5-dichloro-4-fluorophenyl- or 3,4,5-trichlorophenyl-; or
a compound of or formula ID

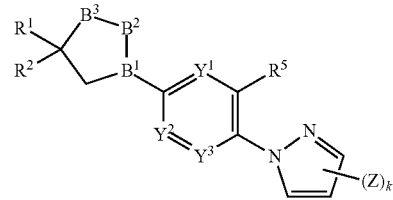

(ID)

wherein
$R^5$ is cyano;
$R^1$ is $CF_3$;
—$B^1$—$B^2$—$B^3$— is —C=N—O— or —C=N—$CH_2$—;
$Y^1$, $Y^2$ and $Y^3$ are CH;
k is 1; and
Z is cyano or trifluoromethyl;
$R^2$ is 3,5-dichlorophenyl-, 3,5-dichloro-4-fluorophenyl- or 3,4,5-trichlorophenyl-.

* * * * *